(12) United States Patent
Osanai et al.

(10) Patent No.: US 7,351,378 B2
(45) Date of Patent: Apr. 1, 2008

(54) NUCLEIC ACID EXTRACTION DEVICE

(75) Inventors: Tsuyoshi Osanai, Saitama (JP); Eiji Yamamoto, Saitama (JP); Katsuhiro Tomaru, Saitama (JP); Junji Fujimoto, Tokyo (JP); Koichi Watanabe, Tokyo (JP); Takahiro Matsuki, Kanagawa (JP); Yukiko Miyamoto, San Diego, CA (US); Ryuichiro Tanaka, Tokyo (JP)

(73) Assignee: Kabushiki Kaisha Yakult Honsha, Tokyo (JP)

( * ) Notice: Subject to any disclaimer, the term of this patent is extended or adjusted under 35 U.S.C. 154(b) by 721 days.

(21) Appl. No.: 10/490,438

(22) PCT Filed: Sep. 27, 2002

(86) PCT No.: PCT/JP02/10035

§ 371 (c)(1),
(2), (4) Date: Mar. 24, 2004

(87) PCT Pub. No.: WO03/029455

PCT Pub. Date: Apr. 10, 2003

(65) Prior Publication Data

US 2004/0248130 A1 Dec. 9, 2004

(30) Foreign Application Priority Data

Sep. 28, 2001 (JP) ............................. 2001-299454

(51) Int. Cl.
*C12Q 1/68* (2006.01)
*C12M 1/02* (2006.01)
*C12M 1/34* (2006.01)

(52) U.S. Cl. ...................... 422/101; 435/6; 435/287.2; 435/270; 436/25.41

(58) Field of Classification Search ............... 435/91.1, 435/6, 287.2, 270; 536/25.4; 436/25.41; 422/101

See application file for complete search history.

(56) References Cited

U.S. PATENT DOCUMENTS 6,235,501 B1 5/2001 Gautsch et al.

FOREIGN PATENT DOCUMENTS

JP 2002-255 A 1/1990

(Continued)

OTHER PUBLICATIONS

Smit, Maarten et al., "Automated Extraction and Amplification of DNA from Whole Blood using a Robotic Workstation and an Integrated Thermocycler", Biotechnology and Applied Biochemistry, vol. 32, No. 2, Oct. 2000, pp. 121-125, XP002313891.

(Continued)

*Primary Examiner*—Jill Warden
*Assistant Examiner*—Christine T. Mui
(74) *Attorney, Agent, or Firm*—Westerman, Hattori, Daniels & Adrian, LLP.

(57) ABSTRACT

The present invention provides an apparatus for extracting nucleic acid from a specimen, including traditionally difficult specimens, in preparation for polymerase chain reaction (PCR) analysis. The apparatus includes: a shaker, a centrifugal separator, a particle supply mechanism for supplying particles of different sizes, a liquid chemical supply mechanism, a conveyance arm for transporting the specimen or tube-containing specimen, and a control means. The control means is designed to shake tubes containing large and small diameter particles and transport the tubes through a centrifuge in order to separate the nucleic acid-containing material from the remainder of the specimen and crush the material to extract the nucleic acid.

4 Claims, 22 Drawing Sheets

FOREIGN PATENT DOCUMENTS

| | | |
|---|---|---|
| JP | 11-215978 | 8/1999 |
| JP | 11-215978 A | 8/1999 |
| JP | 2000-342258 | 12/2000 |
| JP | 2000-342258 A | 12/2000 |
| JP | 2001-017168 | 1/2001 |
| JP | 2001-17168 | 1/2001 |
| JP | 2001-17168 A | 1/2001 |
| JP | 2002-000255 | 1/2002 |
| JP | 2002-255 | 1/2002 |
| WO | WO 90/15148 A1 | 12/1990 |

OTHER PUBLICATIONS

More, M. I. et al., "Quantitative Cell Lysis of Indigenous Microorganisms and Rapid Extraction of Microbial DNA from Sediment", Applied and Environmental Microbiology, vol. 60, No. 5, May 1, 1994, pp. 1572-1580, XP000574303.

Miller, D. N. et al., "Evaluation and Optimization of DNA Extration and Purification Procedures for Soil and Sediment Samples", Applied and Environmental Microbiology, vol. 65, No. 11, Recceived Jul. 1, 1999, pp. 4715-4724, XP002148457.

Kuske, C. R. et al., "small-scale DNA Sample Preparation Method for Field PCR Detection of Microbial Cells and Spores in Soil", Applied and Environmental Microbiology, vol. 64, No. 7, Jul. 1998, pp. 2463-2472, XP002226433.

Supplementary European Search Report dated Jan. 18, 2005, issued in corresponding European Application No. 02 77 0223.

Office Action dated Jan. 6, 2005, issued in corresponding European Application No. 02 770 223.

NUCLEIC ACID EXTRACTION DEVICE

TECHNICAL FIELD

The present invention relates to an apparatus for extracting DNA (deoxyribonucleic acid) from a variety of specimens such as feces, sludge, and the like.

BACKGROUND ART

Recently, it has become possible to perform rapid and precise detection/identification of bacteria relatively easily and conveniently by using a specific PCR primer.

To perform analysis using the PCR (polymerase chain reaction) primer mentioned above (PCR method) when human feces, excreta, sludge, and the like are samples, it is necessary to extract DNA which is easily provided for PCR from the samples.

With prior art technologies, however, actual practice is that the extraction of such a nucleic acid has been performed manually. For the execution of analysis using the PCR primer with respect to samples such as human feces, excreta, sludge, and the like, it has conventionally been requested to automate the step of extracting a nucleic acid from the samples and perform the automated extraction step rapidly and precisely, but the development of such an automatic apparatus and an automated procedure has not been accomplished yet.

The present invention has been proposed in view of the foregoing problems of the prior art technologies. It is therefore an object of the present invention to provide an automated nucleic acid extraction apparatus which extracts a nucleic acid from a specimen from which it has conventionally been considered difficult to extract a nucleic acid, such as feces or sludge, and thereby allows analysis using the PCR method.

DISCLOSURE OF THE INVENTION

A nucleic acid extraction apparatus of the present invention includes: a shaker (shaker 3); a centrifugal separator (5); a particle supply mechanism (8, 9) for supplying plural types of particles (e.g., beads) having different particle diameters; a liquid chemical supply mechanism (11) for supplying a liquid chemical; an arm (which may include a plurality of arms or a single arm depending on cases) (13, 14, 15) for conveying a specimen or a tube (52) having therein the specimen (e.g., feces, sludge, or the like); and control means, wherein the control means is constructed to perform a control operation for shaking the tube (52) supplied with particles each having a large particle diameter and the specimen, putting the tube through the centrifugal separator (5) to separate material (e.g., a fungus body) containing a nucleic acid (DNA) from the specimen, shaking the tube (52) supplied with the separated material containing the nucleic acid (e.g., a fungus body) and particles each having a small particle diameter, and putting the tube through the centrifugal separator (5) to crush the material containing the nucleic acid (e.g., a fungus body) and extract the nucleic acid (Claim 1: FIGS. 1 to 3).

Here, the foregoing control means is constructed to perform a control operation for separating the nucleic acid (DNA) by crushing the material (bacteria) containing the nucleic acid (DNA), recovering the separated nucleic acid (DNA) (recovery by centrifugation using alcohol, e.g., ethyl alcohol and drying), and purifying the recovered nucleic acid by gel filtration chromatography (Claim 2).

In practicing the present invention, the foregoing centrifugal separator preferably has a stop position indicating member (e.g., slit cam 54 with slit 54S) disposed in correspondence with a specified stop position, indicating member detecting means (origin position sensor 5B, e.g., a gap sensor) for detecting the stop position indicating member being at the specified position, driving means (fixed-position stop motor 59) for moving, when the stop position indicating member does not stop at the specified position, the stop position indicating member to the stop position and a rotation transmission mechanism (timing pulley 58, timing belt 5K, and rotor 51) (Claim 3: FIGS. 10 and 11).

This is for constantly stopping the tube supplied with the specimen at a fixed position by using such a structure.

Preferably, the foregoing particle supply mechanism has a rotating member (rotation wheel 85) formed with a cavity portion (blind hole 85H) having a capacity corresponding to a quantity of supplied particles (e.g., large-diameter beads) and disposed in a supply path (88H), the supply path (88H) is extending in a vertical direction and connecting to a passage (82H) underlying a storage unit (hopper 82) for storing the particles (e.g., large-diameter beads) to be supplied, and particle agitating means (e.g., disk 83 provided with pins 84) is provided rotatably in the foregoing storage unit (hopper 82) (Claim 4: FIGS. 4 to 6).

When the rotating member (rotation wheel 85) rotates to connect the passage (82H) underlying the storage unit (hopper 82) to the cavity portion (blind hole 85H) of the rotating member, the particles (e.g., large-diameter beads) to be supplied are filled in the cavity portion (blind hole 85H). When the rotating member (rotation wheel 85) rotates to connect the cavity portion (blind hole 85H) of the rotating member to the underlying supply path (88H), the particles (e.g., large-diameter beads) to be supplied that have been filled in the cavity portion (blind hole 85H) pass/fall through the underlying supply path (88H) to be supplied.

Alternatively, the foregoing particle supply mechanism preferably has a measurement unit (97) for measuring the quantity (given by, e.g., "Capacity of Measurement Unit 97–Volume of Piston 98") of the supplied particles (e.g., small-diameter beads), a supply unit (99) provided under the measurement unit (97), a particle (e.g., small-diameter beads) storage unit (95) provided over the measurement unit (97), a sheet unit (washer 96) formed on a boundary between the particle storage unit (95) and the measurement unit (97), a valve (piston 98) constructed to be vertically movable, open the foregoing sheet unit (96) and close an inlet (nozzle 99S) of the foregoing supply unit when it moves downward, and close the foregoing sheet unit (96) and open the inlet (nozzle 99S) of the foregoing supply unit when it moves upward, and means (solenoid 91, joint 92, spring 93) for vertically moving the valve (piston 98).

When the foregoing valve (piston 98) moves downward to open the foregoing sheet unit (96), particles having relatively small particle diameters (e.g., beads having particles diameters of about 0.1 mm) flow into the measurement unit (97) from the inner circumferential surface (96I) of the sheet unit (washer 96).

Here, the quantity of the particles flowing into the measurement unit (97) corresponds to the value given by "Capacity of Measurement Unit 97–Volume of Piston 98".

A fixed quantity of particles flown into the measurement unit 97 are supplied to the subsequent step as follows.

When the foregoing valve (piston 98) moves upward to open the inlet (nozzle inlet 99S) of the supply unit, the quantity of particles (e.g., beads having particle diameters of about 0.1 mm) corresponding to the value given by "Capacity of Measurement Unit 97−Volume of Piston 98" mentioned above freely fall from the supply unit (nozzle 99) to be supplied to the subsequent step.

In the case of using a plurality of arms (e.g., three types of arms) in the present invention, it is preferable to have a first arm (13) for moving a sample, a chip (specimen), and the like in a rack, a second arm (14) formed integrally with a pump (6) to suck in an unwanted liquid and discard it, and a third arm (15) for moving an object under test between a cooling tub (22) and devices for separation (shaker (3), centrifugal separator (5)).

It will easily be appreciated that a single arm (and an XYZ robot) may also be constructed to play the foregoing role instead of the foregoing first to third arms (including three XYZ robots 24A to 24C).

Since the nucleic acid extraction apparatus of the present invention having the foregoing structure has extracted the nucleic acid by separating the material (e.g., a fungus body) containing the nucleic acid (DNA) from the specimen and crushing the separated material, it becomes possible to easily and reliably extract the nucleic acid even from specimens from which it has conventionally been considered difficult to extract the nucleic acid, such as feces, sludge, and the like.

Alternatively, a nucleic acid extraction apparatus (1A) of the present invention has: a shaker (shaker: 128); a centrifugal separator (118); a particle supply mechanism (112, 114) for supplying plural types of particles (e.g., beads) having different particle diameters; a liquid chemical supply mechanism (separate injection nozzle: 110) for supplying a liquid chemical; a lid attachment/detachment unit (capper: 106) for attaching and detaching a lid (cap) to and from each of tubes (52); and a work table (100), wherein specimens or a plurality of the tubes (52) having therein the specimens (e.g., feces, sludge, and the like) are contained in respective sections (102A to 102D) of a tube containing member (sample rack: 102), the tube containing member (102) can be moved by moving means (XYZ robot: 104) over the work table (100), the foregoing shaker (128), the centrifugal separator (118), the particle supply mechanism (large bead supplier 112, small bead supplier 114), the liquid chemical supply mechanism (110), and the lid attachment/detachment unit (106) are constructed to be capable of simultaneously processing the plurality of tubes, the foregoing particle supply mechanism (112, 114), the liquid chemical supply mechanism (110), and the lid attachment/detachment unit (106) are constructed to be movable between a position immediately over the foregoing work table (100) when giving necessary processing to the tubes in the tube containing member and a position at a distance from the foregoing work table (100), the foregoing nucleic acid extraction apparatus including control means, wherein the control means is constructed to perform a control operation for shaking the tubes (52) supplied with particles each having a large particle diameter and the specimens, putting the tubes through the centrifugal separator (118) to separate a material containing a nucleic acid (DNA) (e.g., a fungus body) from each of the specimens, shaking the tubes (52) supplied with the separated material containing the nucleic acid (e.g., a fungus body) and particles each having a small particle diameter, and putting the tubes through the centrifugal separator (118) to crush the material containing the nucleic acid (e.g., a fungus body) and extract the nucleic acid.

In such a nucleic acid extraction apparatus (1A), the capper (106), the piston pump (108), the separate injection nozzle (110), the large bead supplier (112), and the small bead supplier (114) are constructed to be capable of simultaneously processing the plurality of tubes (which are four in a second embodiment of FIGS. 16 to 22). When necessary processing is to be performed, the foregoing devices (capper 106, piston pump 108, separate injection nozzle 110, large bead supplier 112, and small bead supplier 114) are constructed to move to positions in the vicinity of the work table (100) and perform the necessary processing with respect to the plurality of tubes in the rack (sample rack: 102).

Accordingly, these devices (106, 108, 110, 112, 114) are fixed to allow a significant reduction in the time spent in a nucleic acid extracting operation, compared with the tubes held by the arm or robot which move to the respective positions of the devices on a one-by-one basis such that the necessary processing is performed.

BEST MODE FOR CARRYING OUT THE INVENTION

Figure 1:
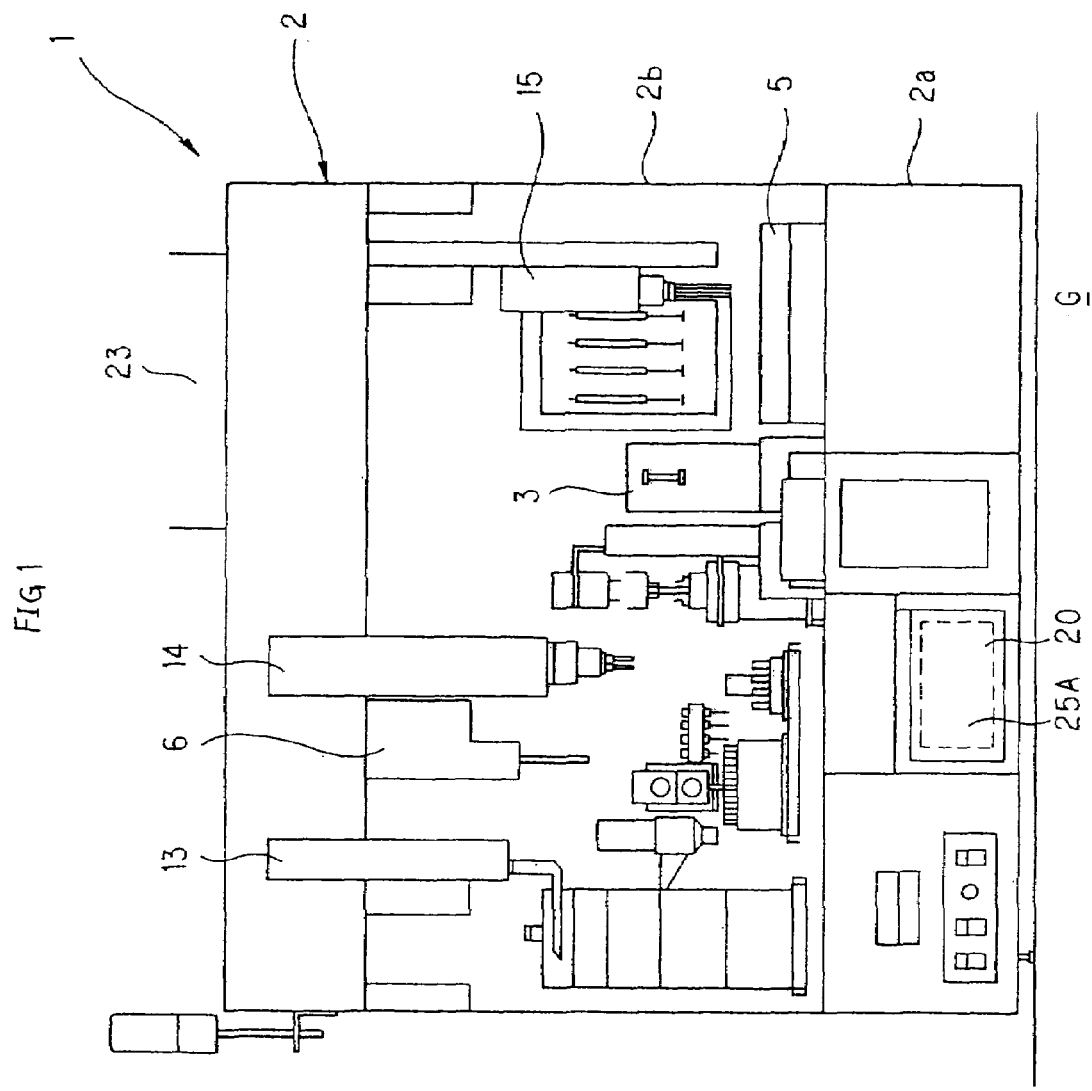
FIG. 1 is a front view showing a structure of a first embodiment of the present invention.

Referring to the accompanying drawings, the embodiments of the present invention will be described herein below.

In the embodiments shown in the drawings, a description will be given to the case where animal feces are specimens (the target of nucleic acid extraction) and a nucleic acid is extracted therefrom.

In the following description, a specimen (sample) or chip indicates a test sample containing a microbe to be analyzed. In the present description, a tube indicates a 2-ml microtube with a screw cap or a 1.5-ml microtube with a screw cap.

A description will be given first to the first embodiment of the present invention with reference to FIGS. 1 to 15.

Figure 2:
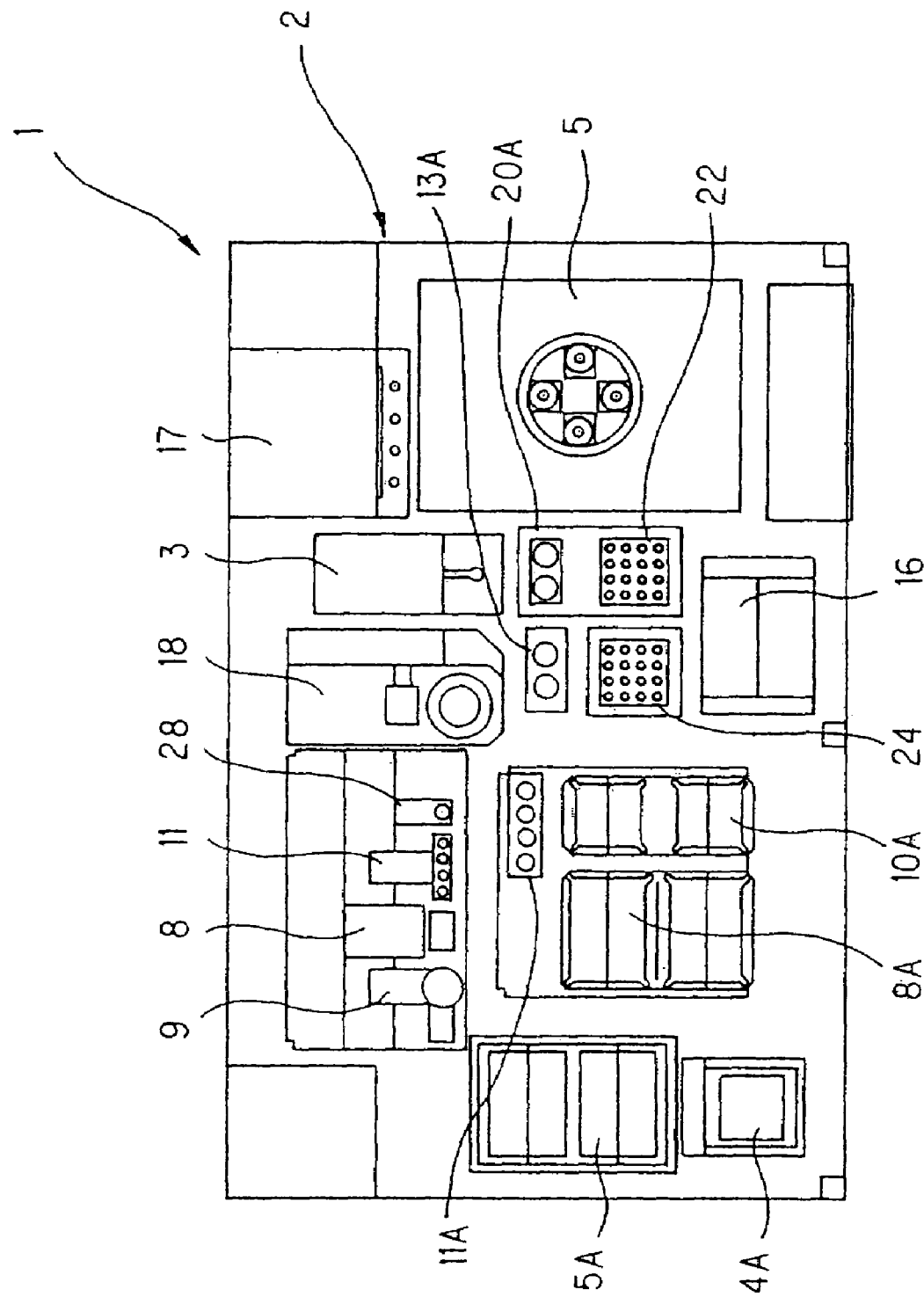
FIG. 2 is a top view of FIG. 1.
Figure 3:
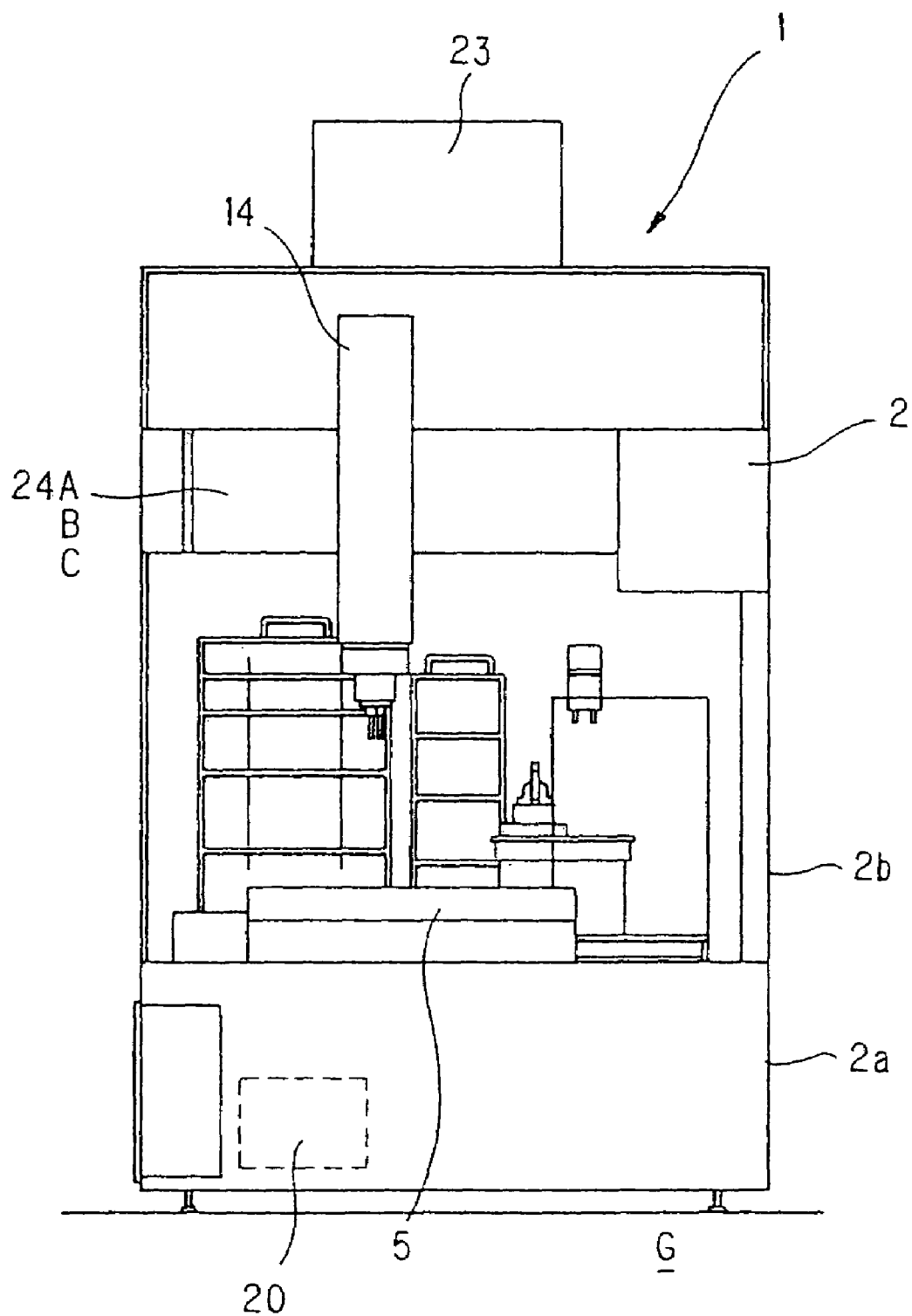
FIG. 3 is a side view of FIG. 1.

FIGS. 1 to 3 show an entire nucleic acid extraction apparatus 1 constructed to perform each of the steps of cleaning, crushing, and separation in one unit to extract a nucleic acid from feces.

In FIG. 1 showing the front of the nucleic acid extraction apparatus 1, FIG. 2 showing the nucleic acid extraction apparatus 1 of FIG. 1 when viewed from the top thereof with a top cover removed, and FIG. 3 showing a side of FIG. 1, the following units are disposed in a casing 2 having a length of 1500 mm, a width of 1200 mm, and a depth of 750 mm and constructed on a floor surface G.

In a lower part 2a of the casing 2, an operation panel 25A and a control unit 20 for automatically operating the entire apparatus are disposed. In an upper part 2b thereof, such units as a tube container box 4A, a container box 5A for a chip as a specimen, a stage for chip 8A, a stage for tube 10A, a reagent stand 11A, a large bead supplier 8, a small bead supplier 9 each as a particle supply mechanism, and a liquid feed nozzle 11 as a liquid chemical supply mechanism are disposed in combination, while a first arm 13 as a manipulator for conveying a tube having therein a reagent (chip) is mounted movably via an XYZ robot 24A attached to the upper portion of the upper part 2b.

In conjunction with the foregoing units, a carrier placement element 28, the reagent (chip) stand 11A, the stage for tube 10A, a capper 18 for the detachment and attachment of a lid to and from a tube, a shaker 3 for agitating a reagent by vibrating a tube, a reagent stand 13A, a stand for cooling reagent 20A, a reagent drier 24, a reagent cooling tub 22, and a waste tub 16 for the disposal of a liquid waste are also disposed in combination in the upper part 2b, while a second arm 14 as a manipulator for moving a reagent (chip) and conveying and discarding an unwanted liquid is mounted movably together with a syringe pump 6 via an XYZ robot 24B attached to the upper portion of the upper part 2b.

In conjunction with the foregoing units, a cylinder pump 17 and a centrifugal separator 5 are also disposed in the upper part 2b, while a third arm 15 as a manipulator associated with the foregoing units and with conveyance between these units is mounted movably via an XYZ robot 24C attached to the upper portion of the upper part 2b.

The categorized operations of the three arms are such that the first arm 13 mainly conveys a sample or chip (specimen) in a rack to the stages, the second arm 14 mainly conducts conveyance to each of the units, i.e., the conveyance of a waste tube and the like from the stages to the capper and from the capper to the suppliers, the shaker, and the cooling tub, while sucking in an unwanted liquid integrally with the cylinder pump and discarding it, and the third arm 15 mainly conveys an object under test between the cooling tub and a device for separation (centrifugal separator).

A well-known commercially available automated device is applicable to each of the arms 13, 14, and 15. Alternatively, the first to third arms 13, 14, and 15 may also be composed of a single arm.

A clean unit 23 for forcibly exhausting the apparatus is provided in the top portion of the casing 2.

Figure 4:
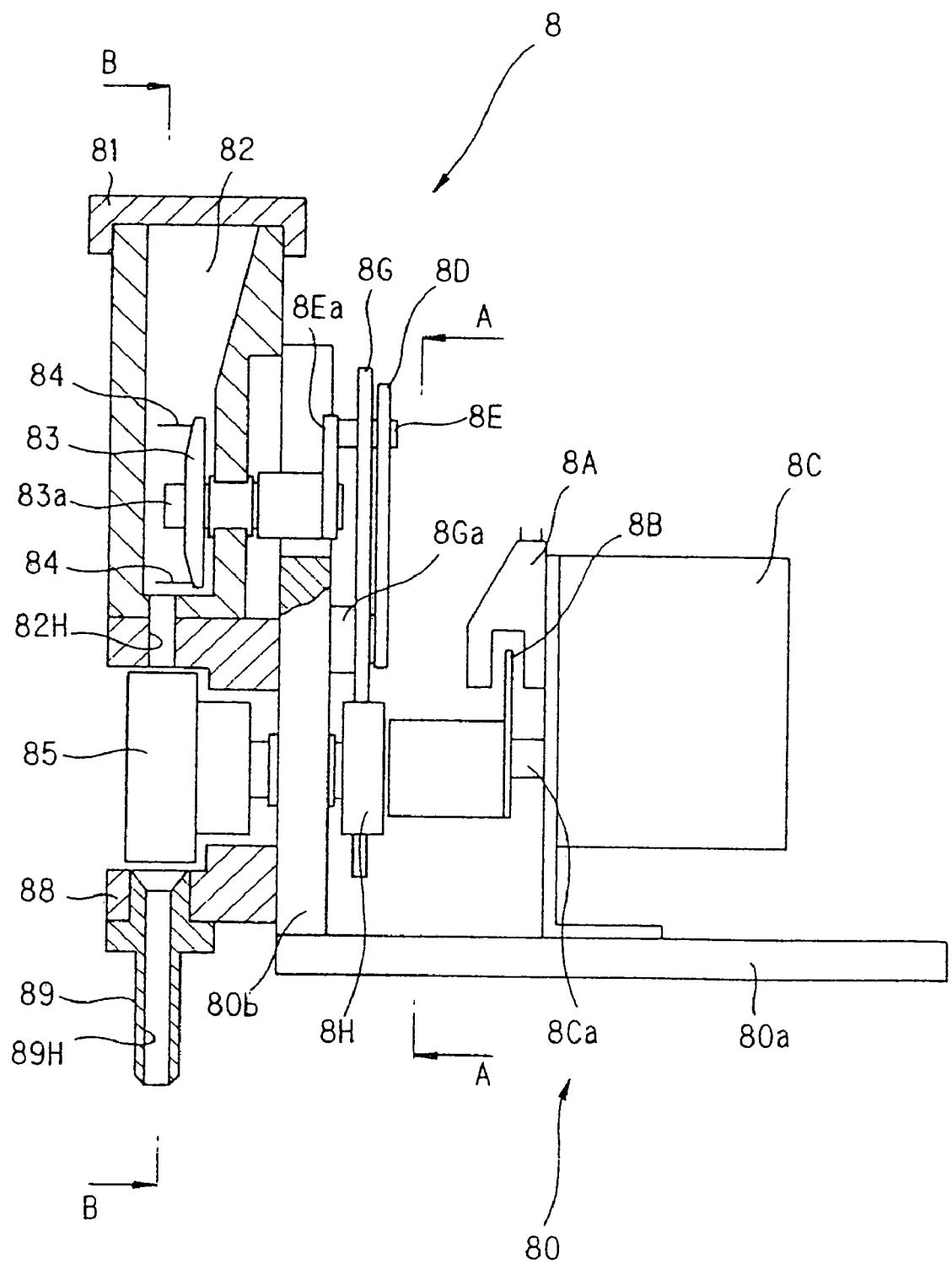
FIG. 4 is a side view of a large-diameter bead supplier.
Figure 5:
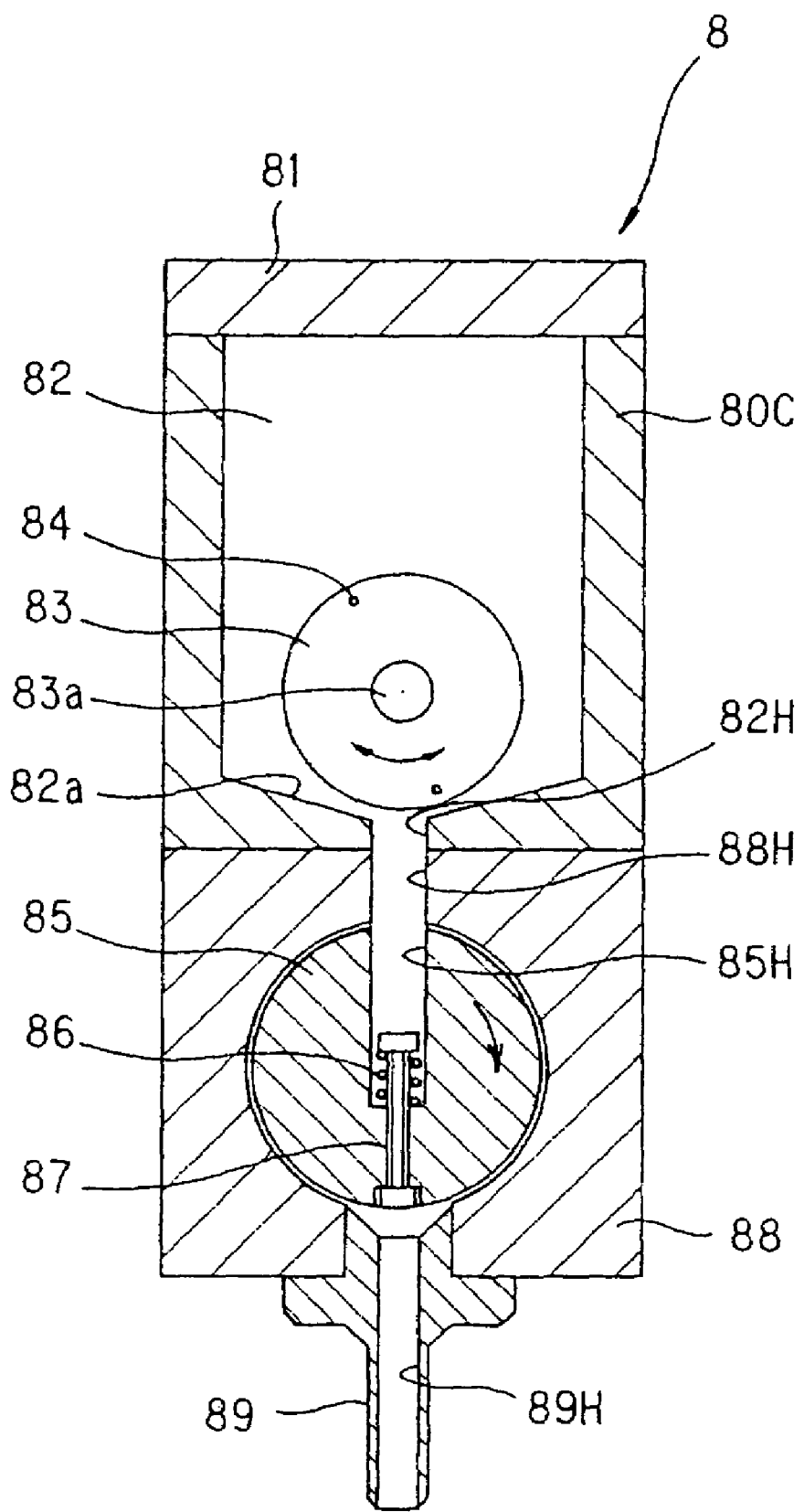
FIG. 5 is a cross-sectional front view taken along the line B-B of FIG. 4.
Figure 6:
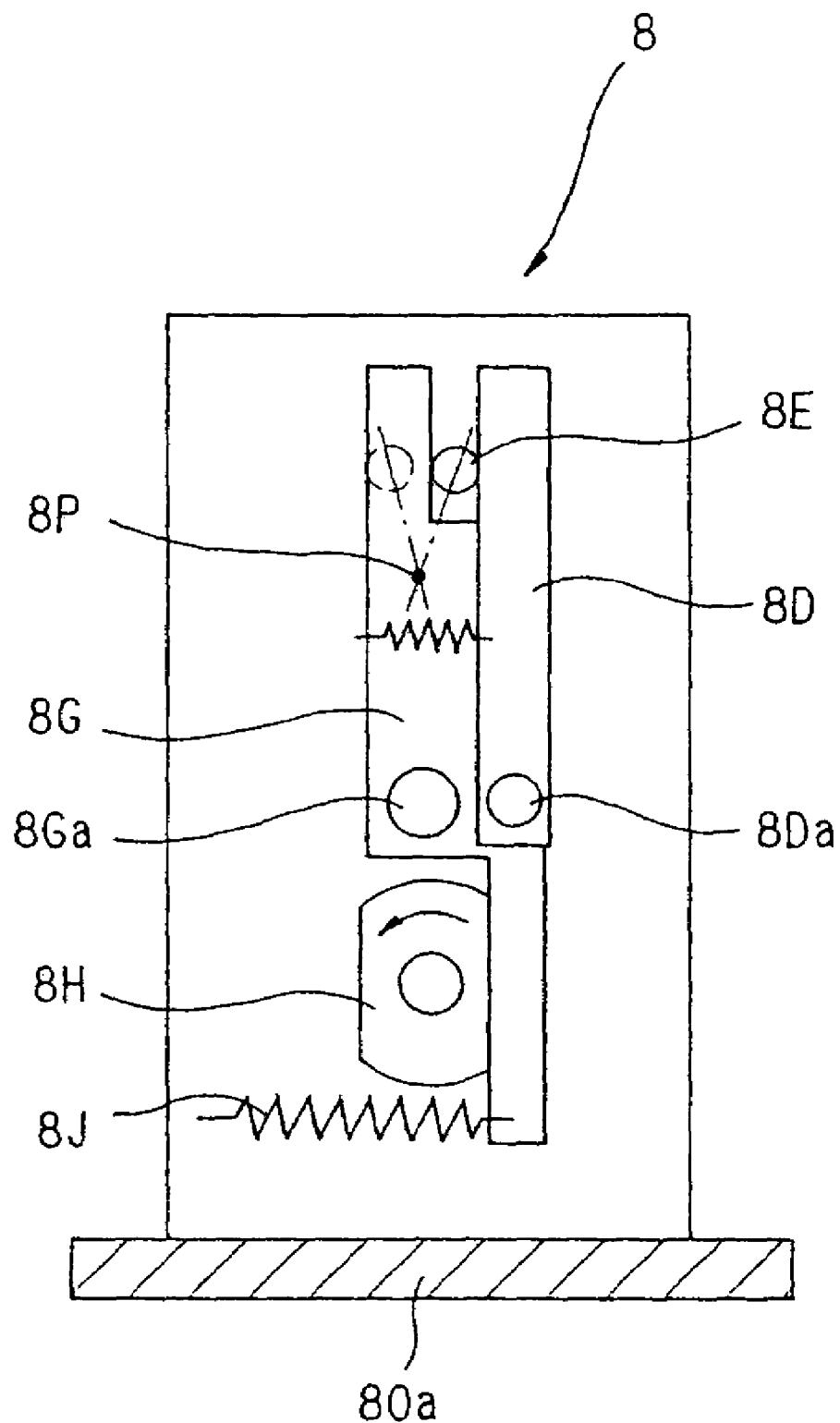
FIG. 6 is a cross-sectional rear view taken along the line A-A of FIG. 4.

FIGS. 4 to 6 show the supplier 8 for large beads (e.g., glass beads having particle diameters of 2 to 3 mm) as the particle supply mechanism. FIG. 4 shows a side of the overall structure, FIG. 5 shows a cross section taken along the line B-B of FIG. 4, and FIG. 6 shows a cross section taken along the line A-A of FIG. 4.

The large bead supplier 8 has a principal portion thereof composed of a motor 8C mounted on a platen 80 consisting of a horizontal base 80a disposed in the lower part 2a (see FIGS. 1 and 3) of the casing 2 and a vertical base 80b, a rotation wheel 85 as a rotating member which slides and rotates in a fixed frame 88, and a disk 83 which rotates in a swinging manner in a storage unit 80C fixed to the upper portion of the fixed frame 88.

The rotation wheel 85 is disposed in a supply path 88H provided in the vertical direction of the fixed frame 88 and coupled to a shaft 8Ca driven by the motor 8C. An origin stop plate 8A for determining the rotating position of the rotation wheel 85 and a cam 8H are mounted on the shaft 8Ca.

The rotation wheel 85 is formed with a cavity portion (blind hole 85H) extending through the core thereof. A double-flanged movable pin 87 connecting to the outside of the wheel 85 is fitted in the bottom portion of the blind hole 85H to be slidable in an axial direction. Springs 86 are attached to the side of the movable pin 87 exposed in the blind hole 87H.

A nozzle 89 provided with a passage 89H is attached to the lower portion of the fixed frame 88. The passage 89 is constructed to connect to the blind hole 85H when the wheel 85 is at a specified bead supply position.

The origin stop plate 8A is constructed to form a pair with a sensor 8A fixed to the horizontal base 80a and define the rotation stop position of the rotation wheel 85.

The cam 8H is disposed to swing a second link 8G using a shaft 8Ga as a core against the springs 8G. A first link 8D using a shaft 8Da provided at the same height as the shaft 8Ga in a horizontal direction is constructed to rotate in a swinging manner integrally with the second link 8G via a pin 8E.

A hopper 82 as a storage unit for storing beads is formed in the storage unit 80C and constructed such that a passage 82H provided in the lower portion of the drooping bottom 82a of the hopper 82 connects to the passage 88H provided in the upper portion of the fixed frame 88.

The disk 83 is provided to have a lower end portion in close proximity to the drooping bottom 82a of the storage unit 82. Pins 84, 84 are provided horizontally in the upper and lower portions of the disk 83, respectively, such that the shaft portion 83a of the disk 83 is supported to freely swing horizontally to the storage unit 80C.

The pin 8E is attached to the rear end portion of the shaft portion 83a via a link 8Ea. The large bead supplier 8 is constructed such that, as the disk 83 rotates in a swinging manner with the swinging motion of the pin 8E, the pins 84, 84 agitate beads in the hopper 82 to allow them to fall freely.

The beads in the hopper 82 are supplied from the nozzle 89 to an external tube as follows.

First, the cam 8H is rotated by the rotation of the motor 8C so that the pin 8E is caused to swing via the first and second links. The swinging motion of the pin 8E rotates the disk 83 in a swinging manner and the beads in the hopper 82 are agitated by the swinging rotation of the pins 84 and 84 so that the beads are allowed to fall downward without stagnation.

Meanwhile, the rotation wheel 85 rotates in one direction, e.g., clockwise and is stopped by the origin stop plate 8B and the sensor 8A at a specified stop position, i.e., at a position at which the blind hole 85H connects to the passages 82H, 88H.

A prescribed number of beads are filled in the bind hole 85H against the springs 86 through the passages 82H, 88H. Then, the rotation wheel 85 rotates halfway to cause the beads in the blind hole 85H to fall into the passage 89H. At this time, the stretching force of the biased springs 86 compensates for a size error between a proper number of beads and contributes to the extraction of the beads.

In this manner, a prescribed number of heads fall to be supplied.

Figure 7:
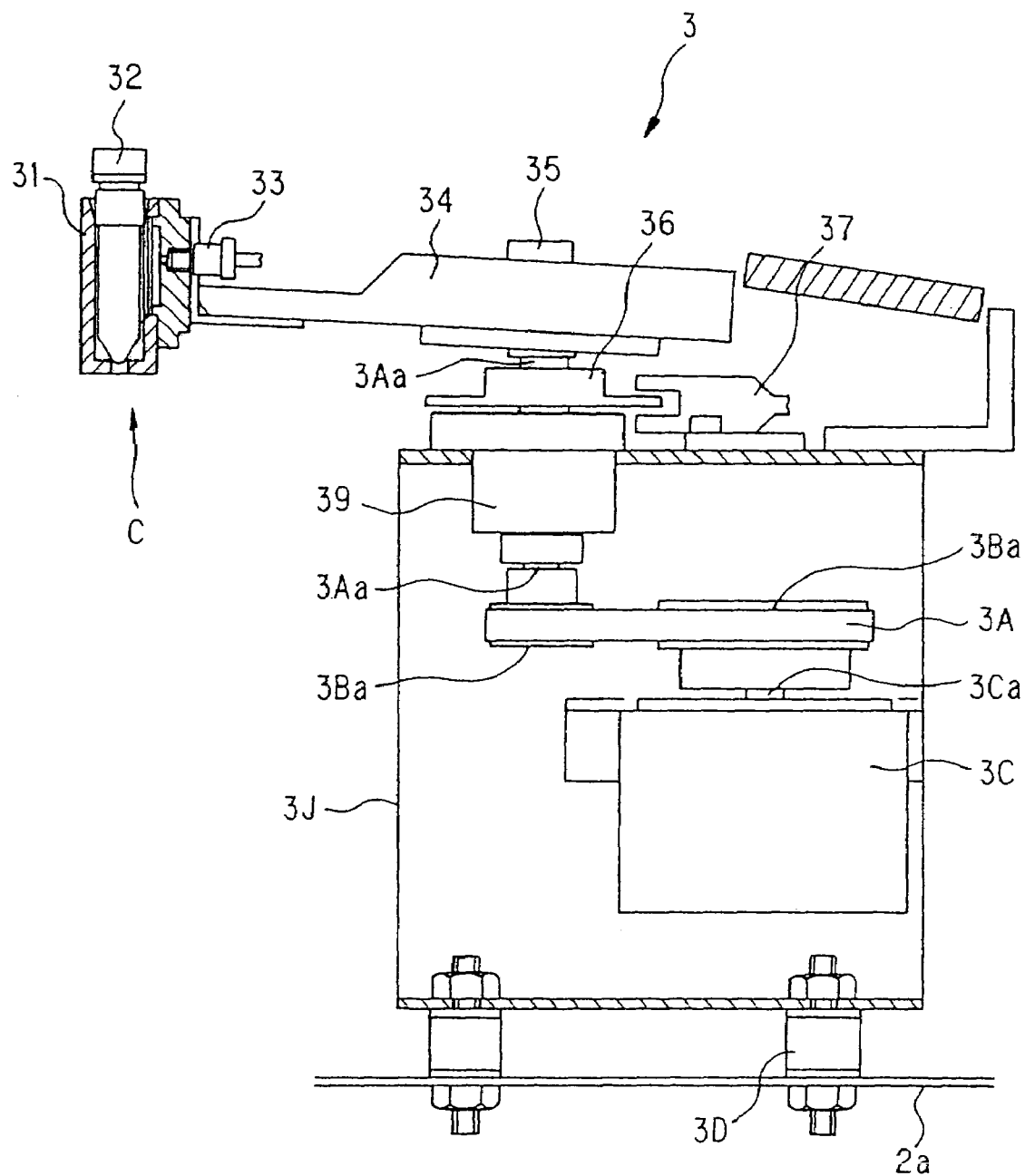
FIG. 7 is a side view of a shaker.
Figure 8:
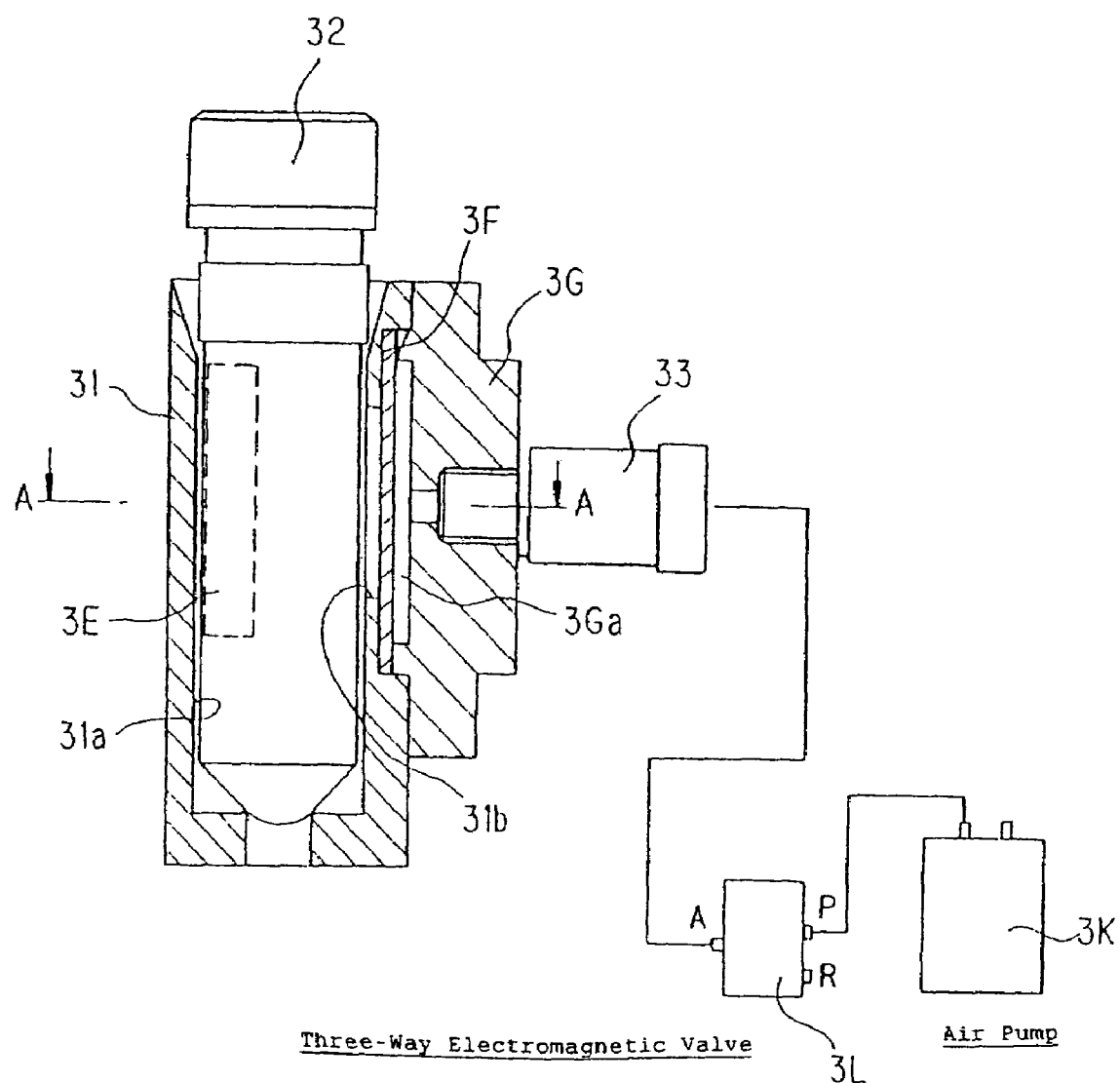
FIG. 8 is an enlarged view of the portion C of FIG. 7.
Figure 9:
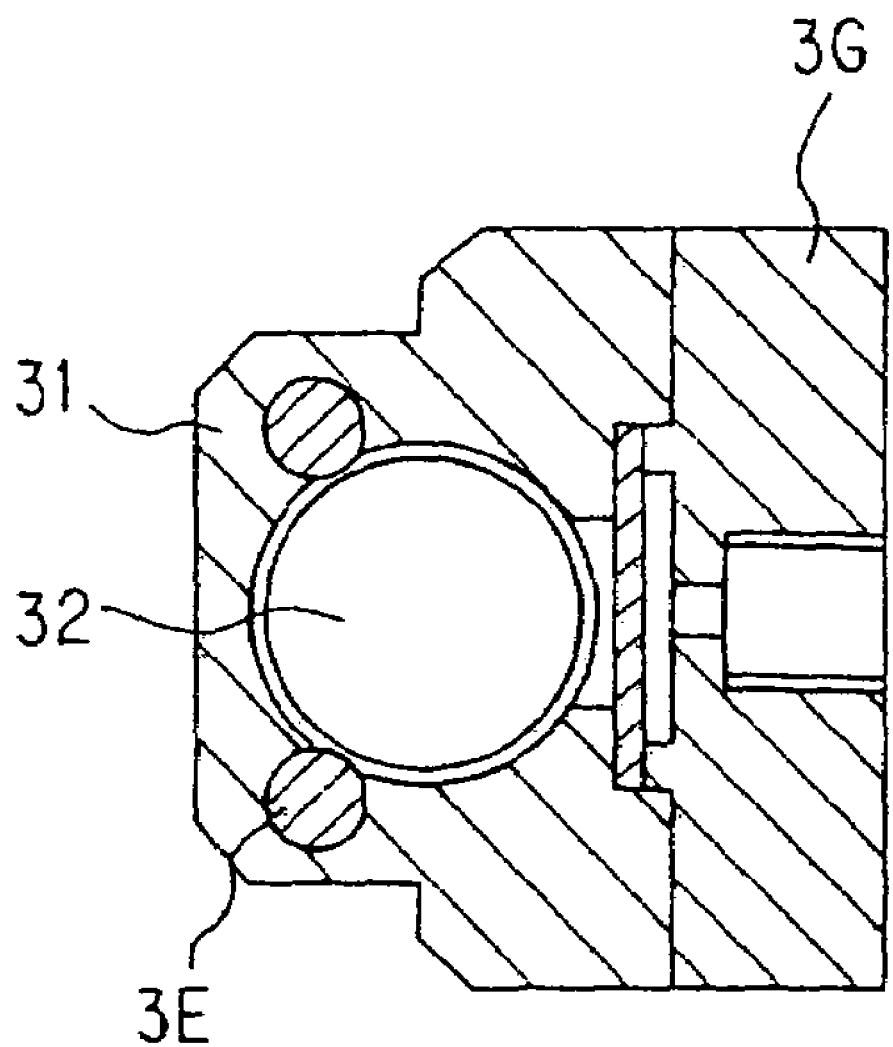
FIG. 9 is a cross-sectional view taken along the line A-A of FIG. 8.

FIGS. 7 to 9 show a shaker 3 of an eccentric-rotation and vertical-vibration type. FIG. 7 shows a side structure thereof, FIG. 8 shows in detail an enlarged portion A of FIG. 7, and FIG. 9 shows a cross section taken along the line A-A of FIG. 8.

The shaker 3 has a principal portion thereof composed of a motor 3C mounted in a base 3J disposed in the lower part 2a (see FIGS. 1 and 3) of the casing 2 via an anti-vibration elastic element 3D, a holder 31 for holding a tube 32 to be shaken, and a shaking lever 34 for agitating a specimen by vigorously shaking the holder 31 in vertical and lateral directions.

A shaft 3Aa is supported by a bearing holder 39 on a shaft 3Ca coupled directly to the motor 3C via pulleys 3Ba, 3Bb and a belt 3A. The shaft 3Aa is provided with an eccentric shaft 35 having an eccentric axis and the shaking lever 34 centering around the eccentric shaft 35 is mounted to incline horizontally.

A slit cam 36 is mounted on the shaft 3Aa. The shaker 3 is constructed such that the rotation stop position of the shaking lever 34 is determined by a fixed-position stop sensor 37 forming a pair with the slit cam 36.

The holder 31 with a cylindrical hole 31a for supporting the tube 32 via a holder cap 3G is fixed to the outer end portion of the shaking lever 34.

On the opposite side of the holder cap 3G, two elastic elements 3E each configured as a cylindrical rod, as illustrated in the drawings, are attached to the cylindrical hole 31a in the vertical direction to protrude radially inwardly.

An elastic plate 3F is provided in intervening relation between the holder cap 3G and a window hole 31b of the holder 31 and a gap 3Ga behind the elastic element 3F is connecting to an air path from a fitting 33 for piping. As shown in FIG. 8, the fitting 33 is connecting to a three-way electromagnetic valve 3L and to an air pump 3K via a piping line.

The shaker 3 having the foregoing structure operates as follows.

The shaking lever 34 is stopped at a specified position by the slit cam 36 and the fixed-position stop sensor 37 and the tube 32 in which a specimen is inserted is fitted into the hole 31a by the arm 14 and the robot 24B. The tube 32 is pressed flexibly by an air from the air pump 3K between the elastic plate 3F and the elastic elements 3E, contained stably, and fixed with proper anti-vibration and shock-resistant properties.

Then, the rotation of the motor 3C adds radial and vertical vibrations to the tube 32 due to the eccentricity and inclination of the shaking lever 34 so that the specimen is agitated.

After the agitation by shaking, the shaking lever 34 stops at the specified position so that the tube 32 is automatically detached or attached by the robot 24B and the arm 14 of FIGS. 1 and 3.

In the present shaker 3, homogenization of a fungus body during cleaning is performed at 1000 rpm or more for 5 seconds or longer. To crush the fungus body and thereby homogenize it, shaking is performed at 1000 rpm or more for 10 seconds or longer. A phenol-chloroform treatment is performed at 3000 rpm for 60 seconds or longer. It is particularly preferred to perform homogenization during cleaning at 1500 rpm or more for about 10 seconds, homogenization after crushing at 4000 rpm to 5000 rpm for about 30 seconds, and the phenol-chloroform treatment at 3000 rpm for about 60 seconds.

Figure 10:
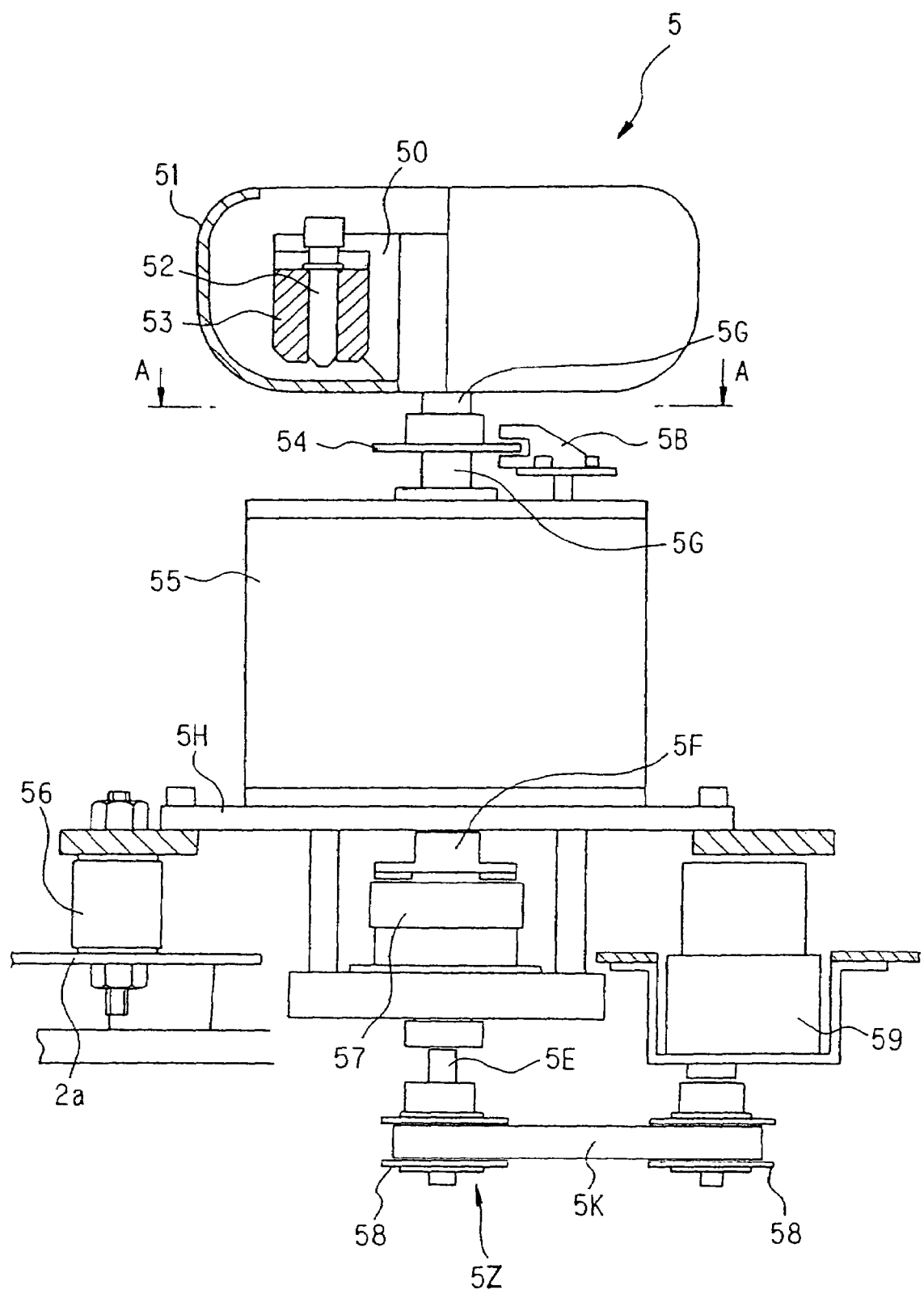
FIG. 10 is a side view of a centrifugal separator.
Figure 11:
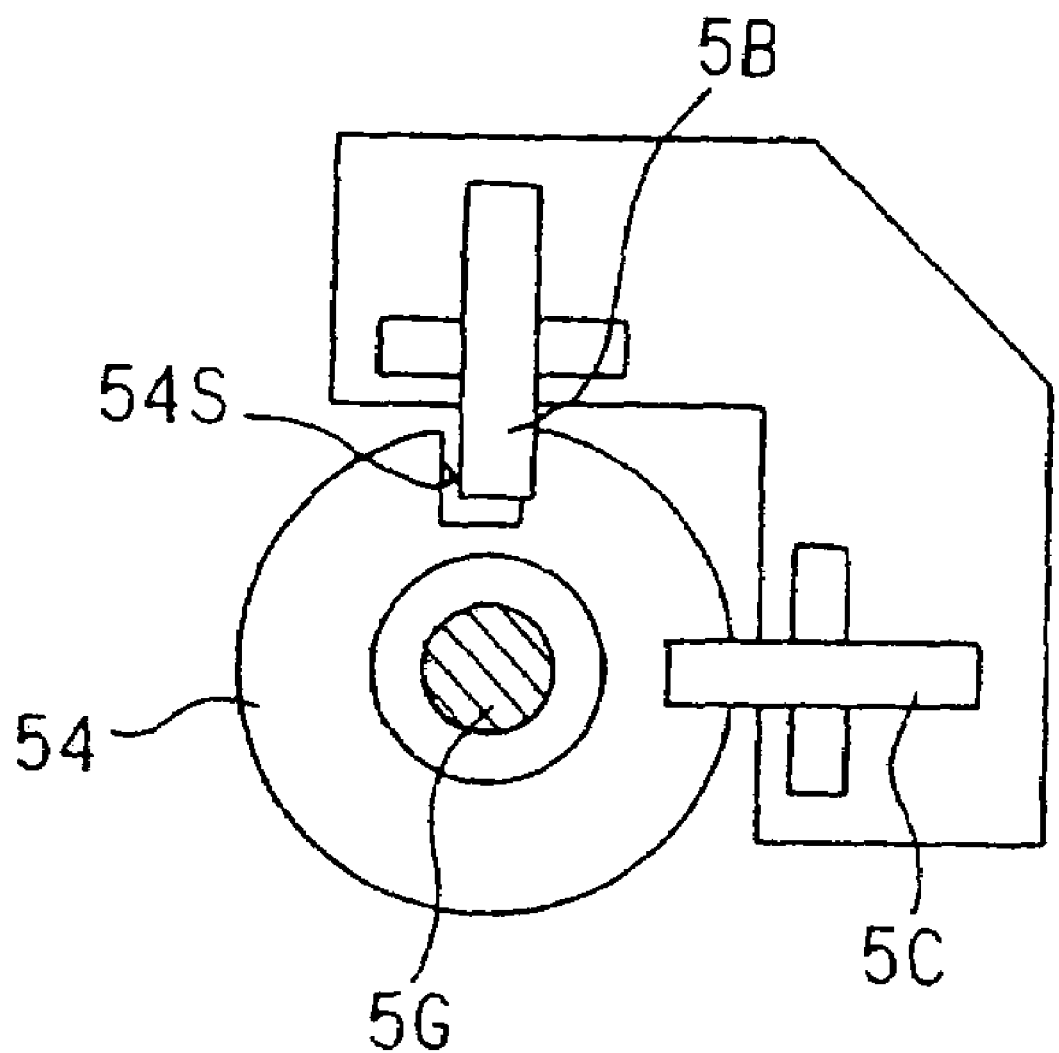
FIG. 11 is a cross-sectional view taken along the line A-A of FIG. 10.

FIGS. 10 to 11 show the centrifugal separator 5 of a swing-rotor type. FIG. 10 shows a side structure and FIG. 11 shows in detail an enlarged cross section taken along the line A-A of FIG. 10.

The centrifugal separator 5 has a principal portion thereof composed of a motor 55 mounted on a base 5H disposed in the lower part 2a (see FIGS. 1 and 3) of the casing 2 via holding a tube 52 to be subjected to centrifugal separation, a fixed-position stop motor 59 as driving means for moving the stop position of the bucket 53 to a specified position, a rotation transmission mechanism for transmitting the rotation of the motor 9, an origin position sensor 5B for detecting the stop position, and the like.

The centrifugal separator 5 is constructed such that a rotor 51 configured as a hollow disk having an open top is fixed to a shaft 5G coupled directly to the motor 55 for centrifugal separation and the plurality of buckets 53 mounted in horizontally conformal relation in the rotor 51 by the support member 50 hold the tubes 52.

Referring also to FIG. 11, a slit cam 54 as a stop position indicating member having a slit 54 is attached to the shaft 5G, while the origin position sensor 5B as indicating member detecting means which detects the position of the slit cam 54 in the rotating direction thereof and a rotation sensor 5C having a 90-degree phase difference between itself and the origin position sensor 5B in a clockwise rotating direction are provided.

A shaft 5F, a clutch 57, and a shaft 5E each as part of the rotation transmission mechanism 5Z of the fixed-position stop motor are connected to the lower portion of the motor 55. The shaft 5E is coupled to the fixed-position stop motor 59 via the rotation transmission mechanism 5Z including a timing pulley 58, a belt 5K, and the timing pulley 58.

The centrifugal separator 5 having the foregoing structure operates as follows.

The rotor 51 and the buckets 53 are stopped at specified positions by the slit cam 54 and the fixed-position stop sensor 5B and the tubes 52 in which the specimens are inserted are fitted into the respective buckets 53 by the arm 15 and the robot 24C of FIGS. 1 and 3.

At this time, the stopping of the rotor 51 and the buckets 53 at the specified positions is performed by using the fixed-position stop motor 59 to precisely compensate for the stop position determined by the motor 55. Specifically, after the motor 55 is stopped, the clutch 57 operates to be coupled to the shaft 5F. Thereafter, the fixed-position stop motor 59 rotates to slightly rotate the rotor 51 and stops it at the position of the fixed-position stop sensor 5B.

By thus stopping the buckets 53 at the specified positions, the tubes 52 can be attached and detached automatically.

The rotation sensor 5C recognizes the 90-degree spaced positions of the buckets 53 in the present example and operates to precisely fit the subsequent tube 52 into the subsequent bucket 53.

After the tubes 52 are inserted into all the buckets 53, the clutch 57 is cut off and the specimens in the tubes 52 are centrifugally separated by the motor 55 with a low-speed rotation for, e.g., nucleic acid extraction or with a high-speed rotation for precipitating a fungus body for cleaning.

During cleaning in the present centrifugal separator 5, centrifugal separation is performed at a number of revolutions of 3000×g or more for 1 minute or longer.

If the structure of the centrifugal separator 5 is scaled up, it is no more necessary to arrange tubes having therein specimens in a quartile configuration as in the present embodiment. For the construction of a one-unit apparatus and the automation thereof, however, a small-size centrifugal separator for four specimens is preferred.

When a spin column (not shown) is attached to the tube 52, it is preferable to provide a depressed portion, i.e., a "counterbore" to prevent interference between the center of the bucket 53 and the spin column of concern, though it is not shown distinctly.

Figure 12:
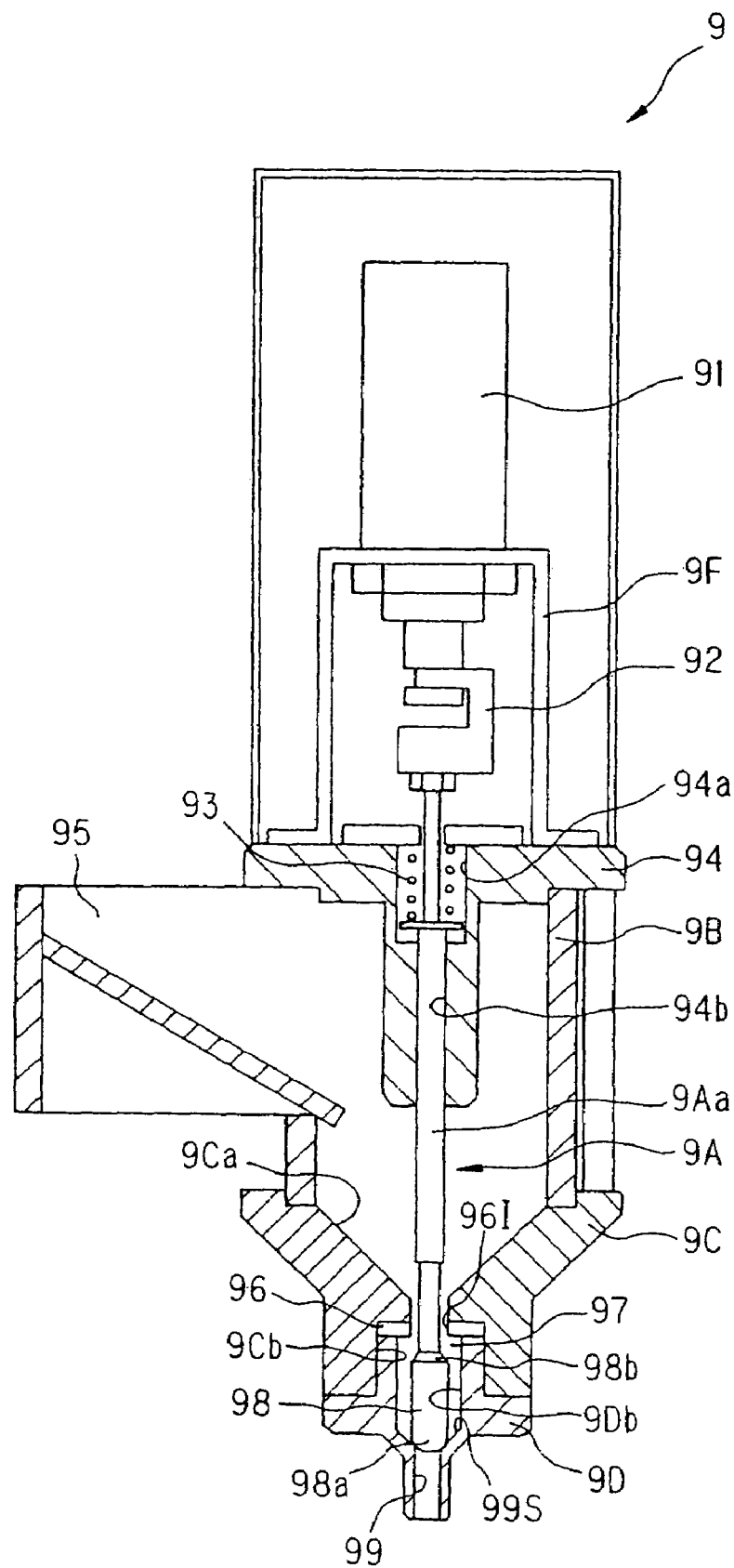
FIG. 12 is a side cross-sectional view of a small-diameter bead supplier.

FIG. 12 shows the supplier 9 for small beads (having particle diameters of, e.g., 0.13 mm) as the particle supply mechanism.

The small bead supplier 9 has a principal portion thereof composed of a hopper element 9B as the particle storage unit for supplying beads from the outside and storing them, a measurement unit 97 for storing a prescribed quantity of beads to be supplied to the tubes and releasing them, a rod-like member 9A with a piston 98 as a valve for the measurement in the measurement unit 97 and the releasing of the beads therefrom, and a solenoid 91 for vertically operating the rod-like member 9A.

The hopper element 9B has a bead supply hole 95 opened to the outside, an upper portion in fixed contact with a bearing 94, and a lower portion in fixed contact with a conical member 9C having a funnel-shaped hole 9Ca.

The nozzle element 9D of the supplier having the measurement unit 97 is inserted in an engagement hole 9Cb formed in the lower portion of the conical member 9C. The hole 9Ca and the measurement unit 97 are connecting to each other via a valve sheet element 96 as a sheet unit. The valve sheet element 96 is formed with an inner circumferential surface 96I serving as a valve hole.

The nozzle element 9D is constructed to have an inner hole 9Db forming the measurement unit 97 and a nozzle hole 99 connecting thereto. The inner hole 9Db and the nozzle hole 99 are connected to each other by a valve sheet 99S.

The bearing 94 is constructed to have a hole 94a in which springs 93 for downwardly pressing the rod-like member 9A are inserted and a hole 94b in which the rod-like member 9A is provided to be vertically movable in the upper portion thereof and support the pull-type solenoid 91 via a support member 9F.

The solenoid 91 is constructed to vertically move the rod-like member 9A via a joint 92.

The rod-like member 9A is constructed to have an upper end portion screwed to the joint 92 to be pressed downward by the springs 93, a center portion 9Aa slidably moving vertically in the hole 94b, and a lower end having the piston 98. The piston 98 is located in the measurement unit 97 and has a lower end portion formed of a spherical valve sheet 98a and an upper end portion formed of a conical valve sheet 98b.

The measurement unit 97 and the piston 98 are constructed to satisfy (Capacity of Measurement Unit 97–Capacity of Piston 8=Quantity of Supplied Beads) and allow a prescribed quantity of beads to be supplied to each of the tubes.

The small bead supplier 9 having the foregoing structure operates as follows.

In the state of FIG. 12, the beads supplied from the bead supply hole 95 are ready in the hopper element 9B to flow into the measurement unit 97 via the inner circumferential surface 96I of the valve sheet 96. At this time, the valve sheets 98a and 99S are in contact with each other so that the nozzle hole 99 is closed.

The capacity of beads in the measurement unit 97 in the foregoing state is given by (Capacity of Measurement Unit 97–Capacity of Piston 8) and a prescribed quantity of beads are reserved.

Then, the solenoid 91 is raised. The piston 98 moves upward to open the valve sheets 98a and 99S, while bringing the valve sheet 98b and the valve sheet element 96 into contact with each other so that they are closed. As a result, beads satisfying "Capacity of Beads=(Capacity of Measurement Unit 97–Capacity of Piston 8)" are supplied from the nozzle hole 99 to the tube.

Then, the solenoid 91 is raised into the state of FIG. 12, whereby a prescribed quantity of beads are allowed to flow into the measurement unit 97.

The control unit 20 as the control means is constructed to have the function of controlling a supply of specimens, measurement, judgment, conveyance of the specimens, agitation, separation, and the like, which is for a sequence of nucleic acid extracting operations to be performed automatically by using the foregoing units.

That is, the control unit 20 is constructed to have the function of extracting a nucleic acid by shaking and agitating the tube supplied with large particle beads and a specimen, separating a material containing the nucleic acid by using the centrifugal separator 5, shaking and agitating the tube supplied with the separated material containing the nucleic acid, particles each having a small particle diameter, and the specimen to cause centrifugal separation and thereby crush the material containing the nucleic acid.

To perform the function, the control unit 20 is connected by a signal line or a control line to each of the fixed-position stop sensor 37 and motor 3C of the shaker 3, the origin position sensor, 90-degree rotating position sensor, and the fixed-position stop motor 59 of the centrifugal separator 5, the sensor 8A and motor 8C of the large bead supplier 8, the solenoid 91 of the small bead supplier 9, the first to third arms 13, 14, and 15, the robot 24A, and the like.

The control unit 20 is also constructed to have the control function of crushing the material containing the nucleic acid to separate the nucleic acid, drying the separated nucleic acid by using alcohol (e.g., ethyl alcohol), and purifying the dried nucleic acid by gel filtration chromatography.

The operation of the nucleic acid extraction apparatus 1 having the foregoing structure will be described in accordance with an automatic operation flow chart of FIGS. 13 to 15.

Figure 13:
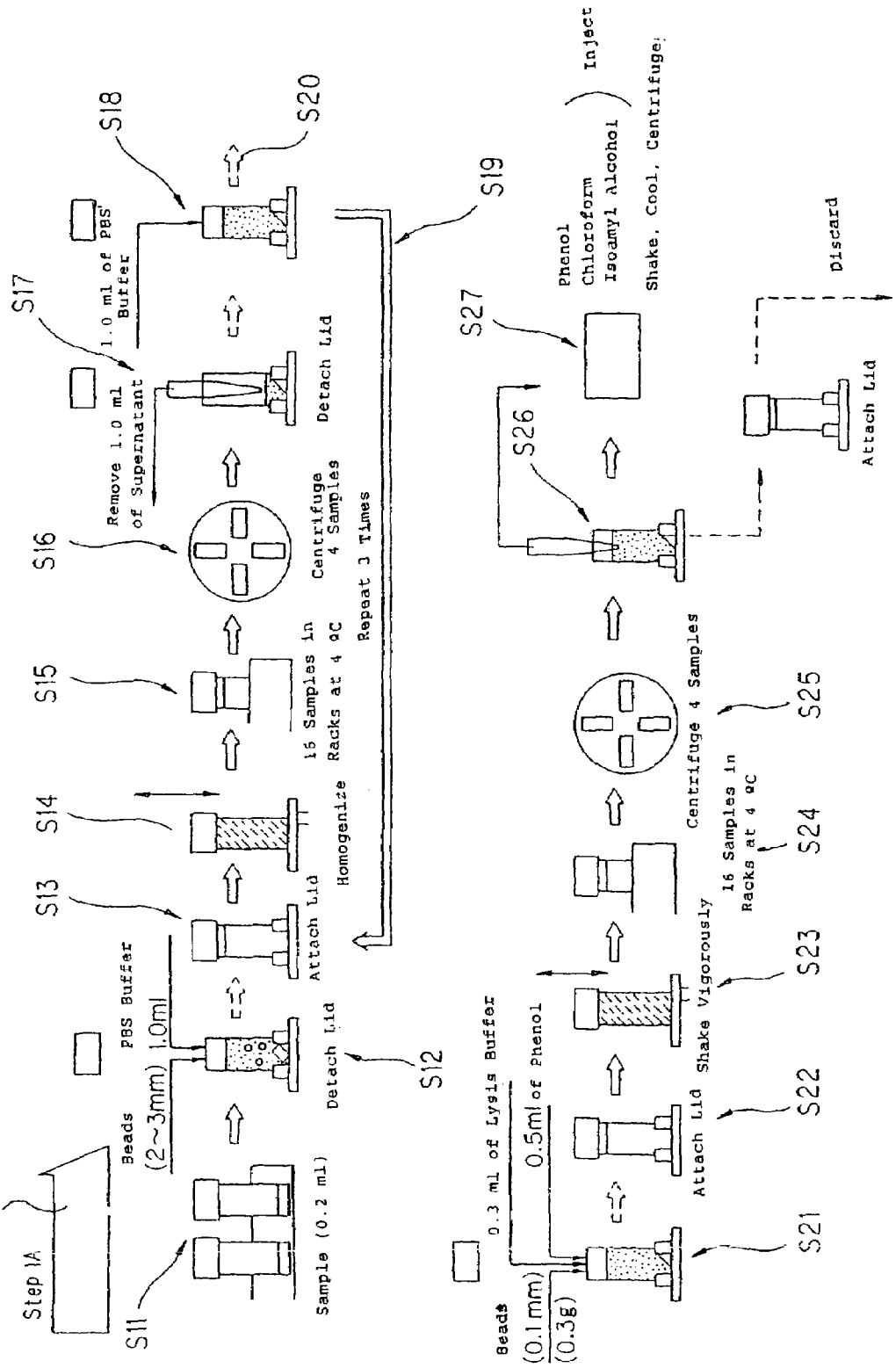
FIG. 13 is a flow chart of an automatic operation mode in a nucleic acid extraction apparatus of the structure shown in FIGS. 1 to 3.

FIG. 13 shows a cleaning step S1A for a specimen. The step S1A is the step of placing beads having large diameters of 2 to 3 mm in a tube having therein a specimen, homogenizing the entire mixture, and performs cleaning to the crushing of a fungus body by agitation, centrifugal separation, and the like.

In Step S11, a tube (2-ml tube) containing a specimen (0.2 ml of specimen) is prepared at 10A by using the first arm 13 and conveyed by using the second arm 14 to the capper 18 and then to the carrier placement element 28.

In Step S12, 1.0 ml of a PBS buffer is injected from the liquid feed nozzle 11 into the tube and large beads (ranging from 2 to 3 mm) are supplied from the large bead supplier 9. In the subsequent steps, the 2-ml tube is used till the end of Step S26.

In Step S13, the tube is conveyed to the capper 18 by using the second arm 14 where it is lidded.

In Step S14, the tube is conveyed to the shaker 3 by using the second arm 14 where it is agitated. By shaking the tube having therein the large-diameter beads, homogenization in which the specimen is floated uniformly in a solvent is accomplished.

In Step S15, the tube after the agitation is conveyed to the cooling tub 22 by using the second arm 14 for the suppression of heat generation resulting from the shaking and the protection of the nucleic acid. Then, cooling to 4° C. is performed.

In Step S16, the cooled tube is conveyed to the centrifugal separator 5 by using the third arm 15, where centrifugal separation is performed. Here, a part of a foreign substance irrelevant to nucleic acid extraction is soluble, compared with the fungus body necessary for nucleic acid extraction, so that the soluble part floats as a supernatant liquid in an upper portion of the solvent.

In Step S17, the tube is retrieved from the centrifugal separator 5 by using the third arm 15, unlidded by using the capper 18, and conveyed to the carrier placement element 28. By using the second arm 14, the supernatant liquid (1.0 ml) in the tube is sucked out and discarded into the waste tub 16. Thus, only the foregoing supernatant liquid containing the foreign substance other than the fungus body, which is irrelevant to nucleic acid extraction, is removed.

In Step S18, a PBS buffer in an amount (1.0 ml) equal to that of the supernatant liquid discarded in Step S17 is added from the liquid feed nozzle 11.

In Step S19, Steps S13 to S18 are repeated three times.

Although Steps S13 to S18 are repeated three times in the present embodiment, the number of times is not limited. By the repetition, the substance other than the fungus body (or a substance related to nucleic acid extraction), i.e., impurities irrelevant to nucleic acid extraction is removed completely from the specimen.

When a specified number of times of repetition (there are cases where repetition is not performed) is completed, the whole process advances to Step S20 (bridge step) and then to Step S21. The following is steps for crushing the fungus body for nucleic acid extraction.

In Step S21, 0.3 ml of a lysis buffer is injected into the tube by using another nozzle of the liquid feed nozzle 11. By using still another nozzle of the liquid feed nozzle, 0.5 ml of phenol is injected. In addition, small beads are supplied from the small bead supplier 9.

This allows the fungus body which was relatively too small to be crushed by using the large beads to be crushed successfully by using the small beads. It is to be noted that the injection of the lysis buffer is performed for easier crushing of the fungus body.

In Step S22, the tube is conveyed to the capper 18 by using the second arm 14, where it is lidded.

In Step S23, the lidded tube is conveyed to the shaker 3 by using the second arm 14, where it is shaken. Collisions between the small-diameter beads and the other large-diameter or small-diameter beads crush the fungus body so that the nucleic acid is released. As a result of the shaking, the tube generates heat.

In Step S14, the tube that has generated heat as a result of Step S23 is conveyed to the cooling tub 22 by using the second arm 14 for the protection of the nucleic acid, where it is cooled at 4° C.

In Step S25, the cooled tube is attached to the centrifugal separator 5 by using the third arm 15 and subjected to centrifugal separation. In this case, the nucleic acid is soluble (water-soluble) so that it floats as a supernatant in the upper region of the solvent and is therefore easily separable.

In Step S26, the tube is retrieved from the centrifugal separator 5 by using the third arm 15 and conveyed to the carrier placement element 28. Here, the supernatant liquid is pipetted and conveyed to another tube rack. Then, the nucleic acid is processed in the subsequent steps.

The waste liquid precipitated in the tube is discarded into the waste tub 16 together with the tube.

In Step S27, the supernatant liquid sucked in by pipetting is injected into another tube not shown and a solution mixture of phenol, chloroform, and isoamyl alcohol is further injected. The tube is subjected to shaking by the shaker 3 without a supply of the beads (either large or small beads), cooled in the cooling tub 22, and further subjected to centrifugal separation by the centrifugal separator 5.

This is the step for denaturing protein, not for crushing the fungus body by using the beads. The tube is retrieved from the centrifugal separator 5 and conveyed to the carrier placement element 28, where a supernatant liquid is pipetted and moved into another 1.5-ml tube (or a rack in which the tube is set). Then, in the subsequent step, an alcohol precipitation process is performed. The whole process advances to the following alcohol precipitation step of FIG. 14.

Figure 14:
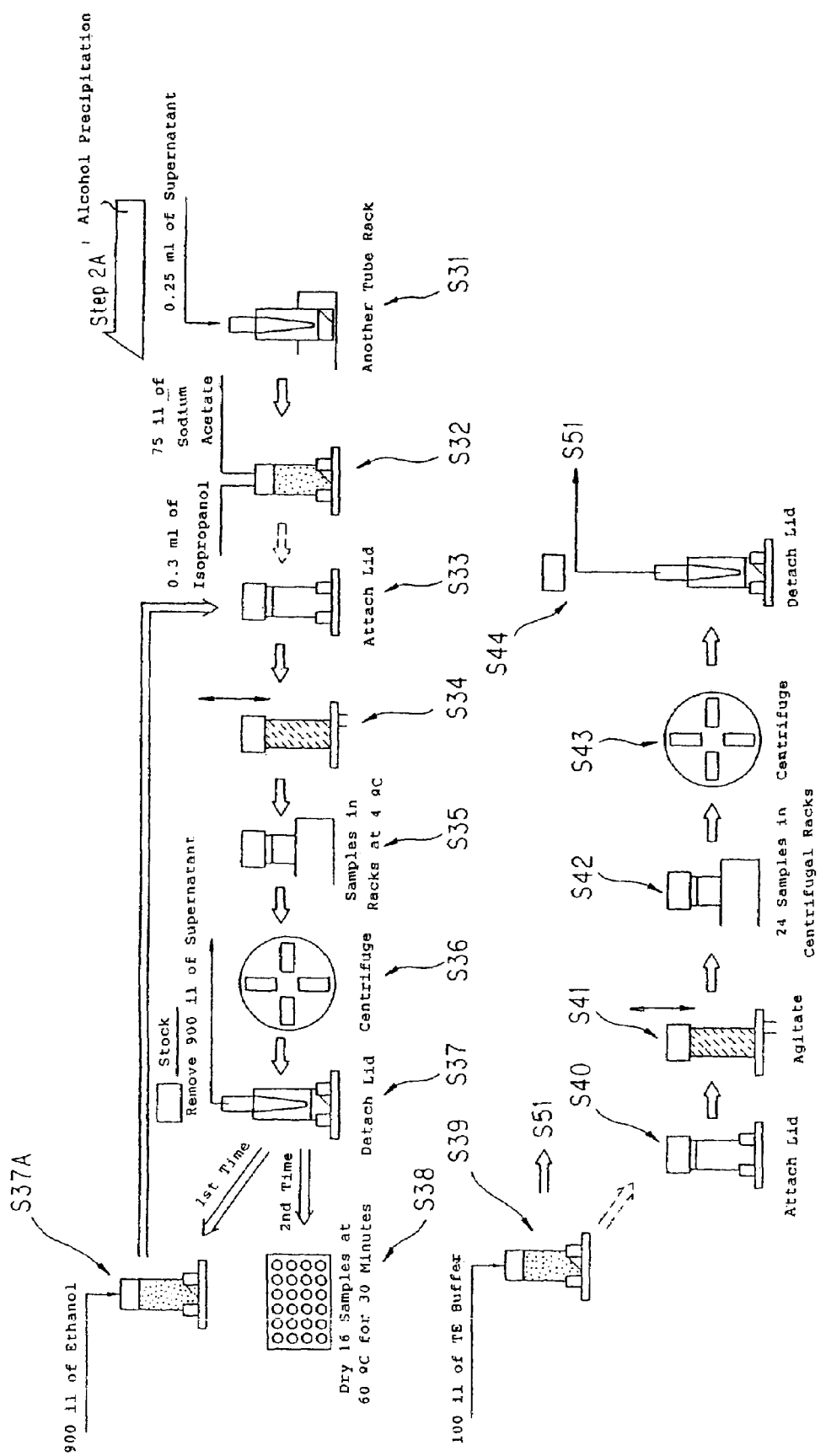
FIG. 14 is a flow chart of the automatic operation mode in the same nucleic acid extraction apparatus as in FIG. 13, which shows steps subsequent to FIG. 13.

FIG. 14 shows an alcohol precipitation step S2A subsequent to Step S27 described above, in which the nucleic acid is precipitated in alcohol and extracted. A precipitation obtained in the step S2A is in a state in which the nucleic acid is precipitated as a solid.

Step S31 shows the state of the protein denatured in Step S27. Herein below, a tube having a 1.5-ml diameter will be used as described above.

In Step S32, 0.3 ml of isopropanol and 75 il of 1N sodium acetate are injected at the carrier placement element 28. By using isopropanol as a solvent, the nucleic acid can be precipitated efficiently.

It can be considered that, once the nucleic acid is precipitated, there will be no refloating so that isopropanol is used only in the first step and ethanol is used in the second and subsequent repetitive steps, which will be described later. Ethanol is easy to evaporate and dry the nucleic acid.

In Step S33, the tube is conveyed to the capper 18 by using the second arm 14, where it is lidded.

In Step S34, the lidded tube is conveyed to the shaker 3 by using the second arm 14, where it is shaken.

In Step S35, the tube the content of which has been homogenized by the shaking is cooled and, for the protection of the nucleic acid, the tube after the shaking is conveyed to the cooling tub 22 by using the third arm 15, where it is cooled at 4° C.

In Step S36, the cooled tube is conveyed to the centrifugal separator 5 by using the third arm 15, attached thereto, and subjected to centrifugal separation. In combination with the shaking in Step S35, the centrifugal separation provides sufficient contact between the nucleic acid and isopropanol so that a specified reaction is performed.

In Step S37, the tube is retrieved from the centrifugal separator 5 by using the third arm 15, unlidded by using the capper 18, and conveyed to the carrier placement element 28. Here, the nucleic acid has been precipitated by the action of isopropanol so that there is no nucleic acid in a supernatant liquid. Then, the supernatant liquid in the tube is sucked in (900 il) by using the second arm 14 and discarded in the waste tub 16. The whole process then advances to Step S37A.

In Step S37A, 70% ethanol (900 il) is added to the tube and Steps S33 to S37 are repeated. In contrast to ethanol which is easy to evaporate and dry, isopropanol allows easy precipitation of the nucleic acid. It can be considered that, once the nucleic acid is precipitated, there will be no refloating so that isopropanol is used only at the initial stage of Step S32 and 70% ethanol is used at the stage of Step S37A.

Then, the whole process advances to Step S38.

In Step S38, the tube from which the supernatant liquid has been discarded is conveyed to the drier 24 by using the second arm 14, where it is dried at 60° C. for 30 minutes or longer.

In Step S39, 100 il of a TE buffer (10 mM Tris-Hcl, 1 mM EDTA pH 8.0) is added.

Figure 15:
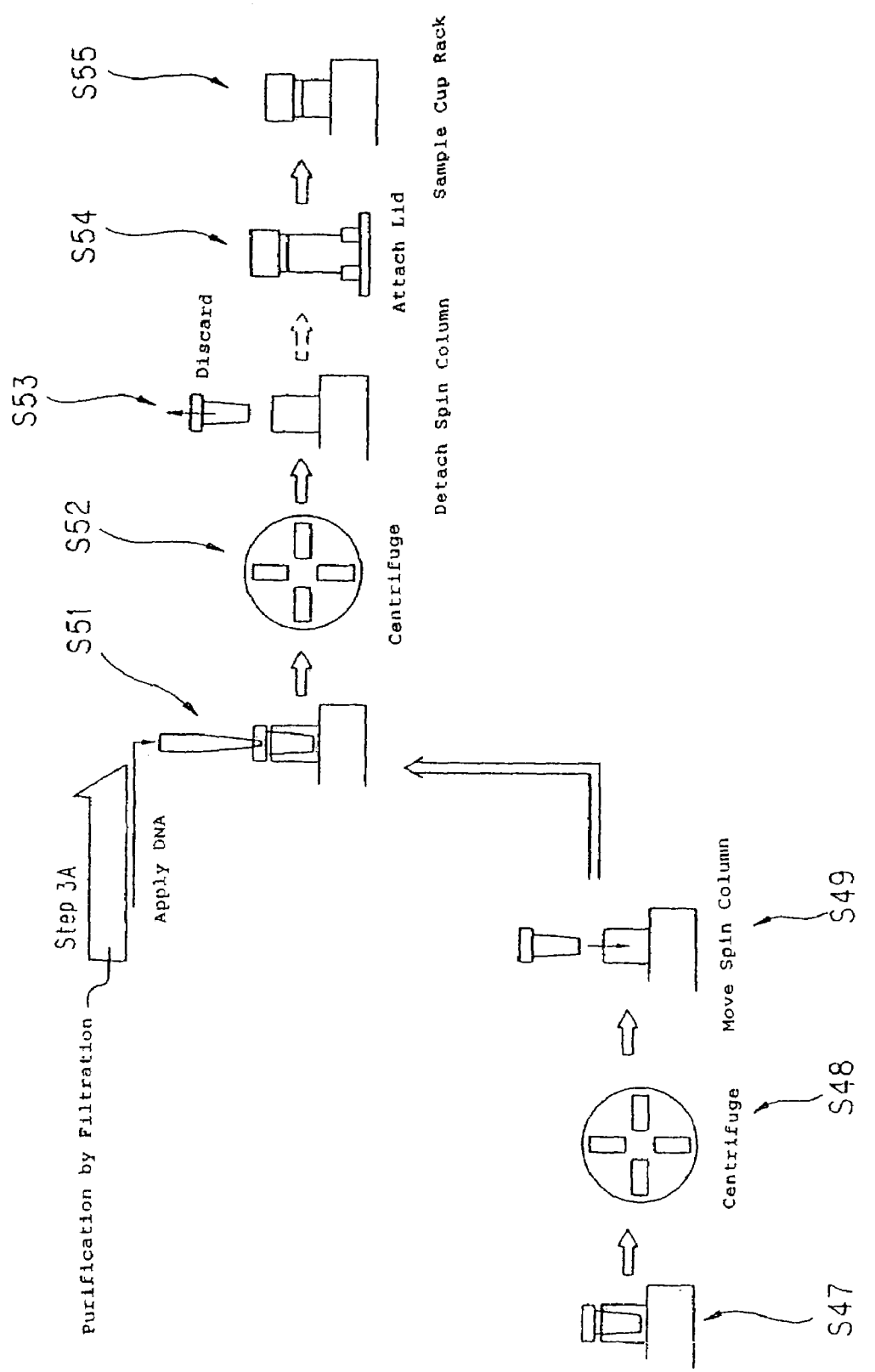
FIG. 15 is a flow chart of the automatic operation mode in the same nucleic acid extraction apparatus as in FIGS. 13 and 14, which shows steps subsequent to FIG. 14.

Then, the whole process advances to a purification step S3A using filtration of FIG. 15.

The steps subsequent to Step S51 are performed by gel filtration chromatography. Since a nucleic acid corresponds to large molecules, the moving speed thereof is high.

In Step S51, the result of Step S39 is directly pipetted by using the second arm 14. Alternatively, it is also possible to perform shaking, centrifugal separation, and the injection of the nucleic acid in the following Steps S40 to S40, instead of pipetting. The reference numerals of the arms to be used are omitted.

In Step S40, a lid is attached by using the capper 18.

In Step S41, shaking is performed by using the shaker 3.

In Step S42, attachment to the centrifugal separator 5 is performed.

In Step S43, centrifugal separation is performed.

In Step S44, the lid is detached and pipetting is performed so that the nucleic acid is moved to Step S51.

Prior to Step S51, Steps S47 to S49 are performed to bring a gel filtration column (or a spin column) into the state of Step S51.

In Step S47, a buffer and a porous filler are filled in the spin column. Commercially available products may be used appropriately.

In Step S48, centrifugal separation is performed by using the centrifugal separator 5 to separate the buffer and the filler into lower and upper regions, respectively.

In Step S49, the spin column is moved and attached.

Then, the whole process advances to Step S51 as the gel filtration step.

In Step S52, the nucleic acid is separated into the lower region by the centrifugal separator 5. Since the nucleic acid corresponds to large molecules, the moving speed thereof is high so that it easily reaches the lower region. Since the other molecules move in trenches in the filler, they require a long time to move so that it is difficult for them to reach the lower region.

In Step S53, the spin column in which "the other small molecules" are present is detached and discarded into the extracted state.

In Step S54, the tube is lidded.

In Step S55, the tube is conveyed to a specified rack and placed in fixed relation, whereby the sequence of operations are completed.

A description will be given next to the second embodiment of the present invention with reference to FIGS. 16 to 22.

Although the tubes are processed on a one-by-one basis in the first embodiment of FIGS. 1 to 15, a plurality of tubes (which are four in FIGS. 16 to 22) are processed simultaneously in the second embodiment of FIGS. 16 to 22.

A description will be given first to a structure of the second embodiment with reference to FIG. 16.

Figure 16:
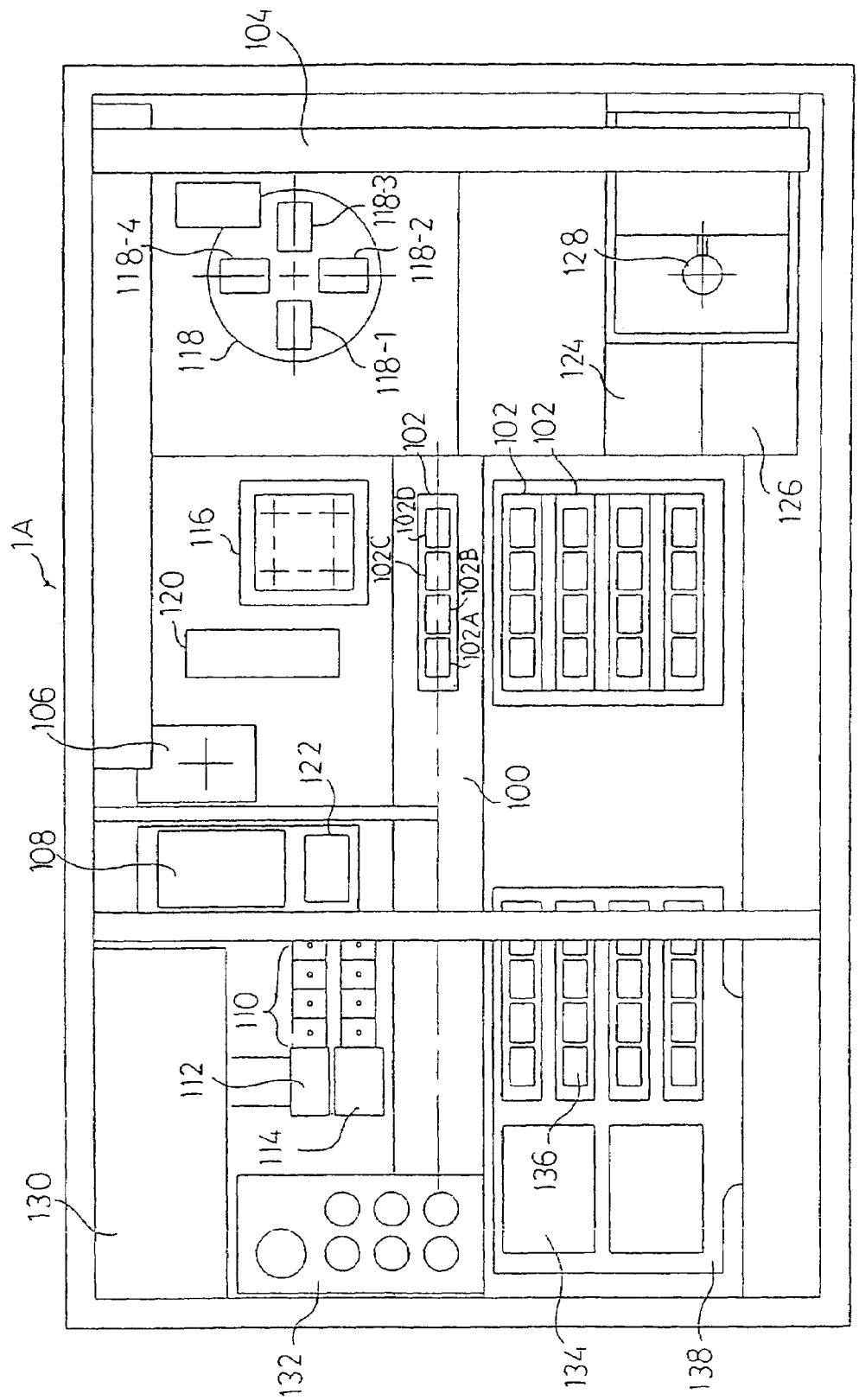
FIG. 16 is a top view showing a structure of a second embodiment of the present invention.

In FIG. 16, an entire nucleic acid extraction apparatus according to the second embodiment is represented by a reference numeral 1A.

In the center portion of the nucleic acid extraction apparatus 1A, a work table 100 is provided. The nucleic acid extraction apparatus 1A is constructed such that racks 102 move over the work table 100. Each of the racks 102 is provided with four sections 102A to 102D and four tubes (not shown in FIG. 16) are contained in each of the four sections 102A to 102D.

The racks 102 are constructed to move over the work table 100 by using an XYZ robot 104.

In the state shown in FIG. 16, a capper 106, a piston pump 108, a separate injection nozzle 110 (corresponding to the liquid feed nozzle 11 as the liquid chemical supply mechanism in the first embodiment), a large bead supplier 112, and a small bead supplier 114 are provided at positions slightly apart from the work table 100.

In the first embodiment of FIGS. 1 to 15, these devices are fixed and the tube held by the arm or robot moves to the position of each of the devices in the manner described above. In the second embodiment shown in FIGS. 16 to 22, however, the foregoing devices (the capper 106, the piston pump 108, the separate injection nozzle 110, the large bead supplier 112, and the small bead supplier 114) move to positions in the vicinity of the work table 100 and perform necessary processing with respect to the tubes in the rack 102.

In addition, the capper 106, the piston pump 108, the separate injection nozzle 110, the large bead supplier 112, and the small bead supplier 114 are constructed to be capable of simultaneously processing the four tubes, as described above.

As for the other structure and operation/working-effect, they are the same as in the first embodiment of FIGS. 1 to 15.

As for a detailed structure of the capper 106, it will be described later with reference to FIGS. 17 and 18.

In FIG. 16, the nucleic acid extraction apparatus 1A has a drier 116 at a position adjacent to the work table 100. A centrifugal separator 118 is provided adjacent to the drier 116.

The centrifugal separator 118 has a structure similar to that of the centrifugal separator 5 used in the first embodiment of FIGS. 1 to 15. In contrast to the four buckets of the centrifugal separator 5 of the first embodiment which contain four tubes on a one-by-one basis, the four buckets 118-1 to 118-4 of the centrifugal separator 118 shown in FIGS. 16 to 22 contain the respective sections 102A to 102D of the sample rack 102 on a one-by-one basis. In other words, the centrifugal separator 118 is constructed such that four tubes are contained in each of the four buckets 118-1 to 118-4 thereof.

The centrifugal separator 118 has a cooling function for maintaining the inside thereof (at least the insides of the buckets 118-1 to 118-4) at a low temperature (e.g., 4° C., though it is not shown distinctly. Such a cooling function can be achieved by using a well-known commercially available device.

A lid rack 120 adjoins the drier 116.

A vessel 122 (corresponding to the waste tub 16) for the disposal of a liquid waste and a discarded chip (the chip will be described later with reference to FIG. 21) is provided at a position in the piston pump 108 closer to the work table 100.

The vessel for the disposal of the tubes is denoted by a reference numeral 124 in FIG. 16. A bucket container vessel 126 for containing used buckets is provided adjacent the vessel 124. A shaker 128 is provided at a position adjacent the vessels 124 and 126. The structure and operation/working-effect of the shaker 128 are the same as those of the shaker 3 used in the first embodiment of FIGS. 1 to 15 except that it simultaneously shakes four tubes.

In FIG. 16, a reference numeral 130 denotes a syringe pump, a reference numeral 132 denotes a bottle rack for supplying various chemical agents, a reference numeral 134 denotes a region on which a chip (which will be described later with reference to FIG. 21) is placed, a reference numeral 136 denotes buckets for tubes which are for placing four tubes in each of the sections 102A to 102D of the rack 102, and a reference numeral 138 denotes a table on which the chip placement area 134 and the buckets 136 . . . for tubes are placed.

Figure 17:
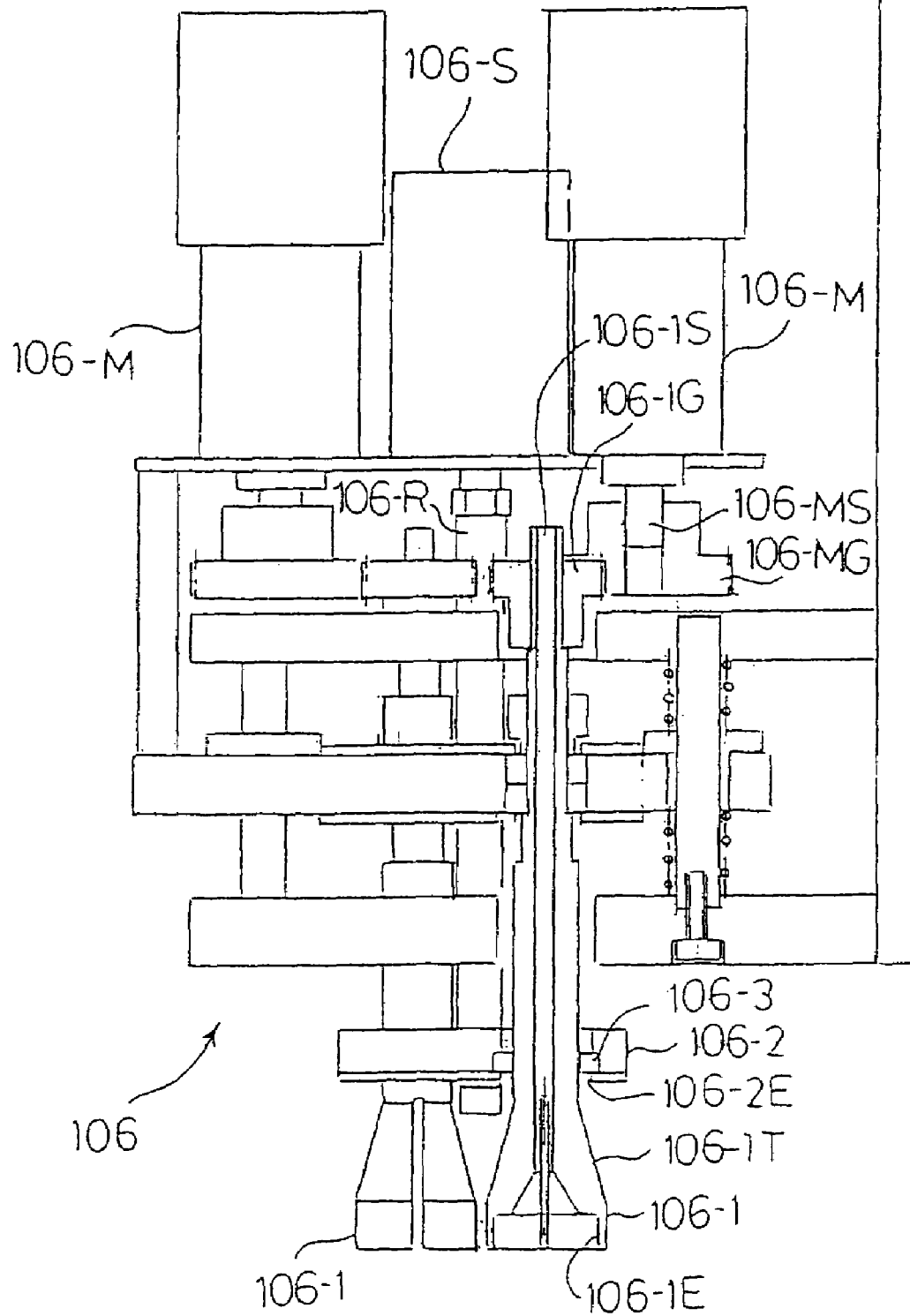
FIG. 17 is a partially cross-sectional front view of a capper used in the second embodiment.
Figure 18:
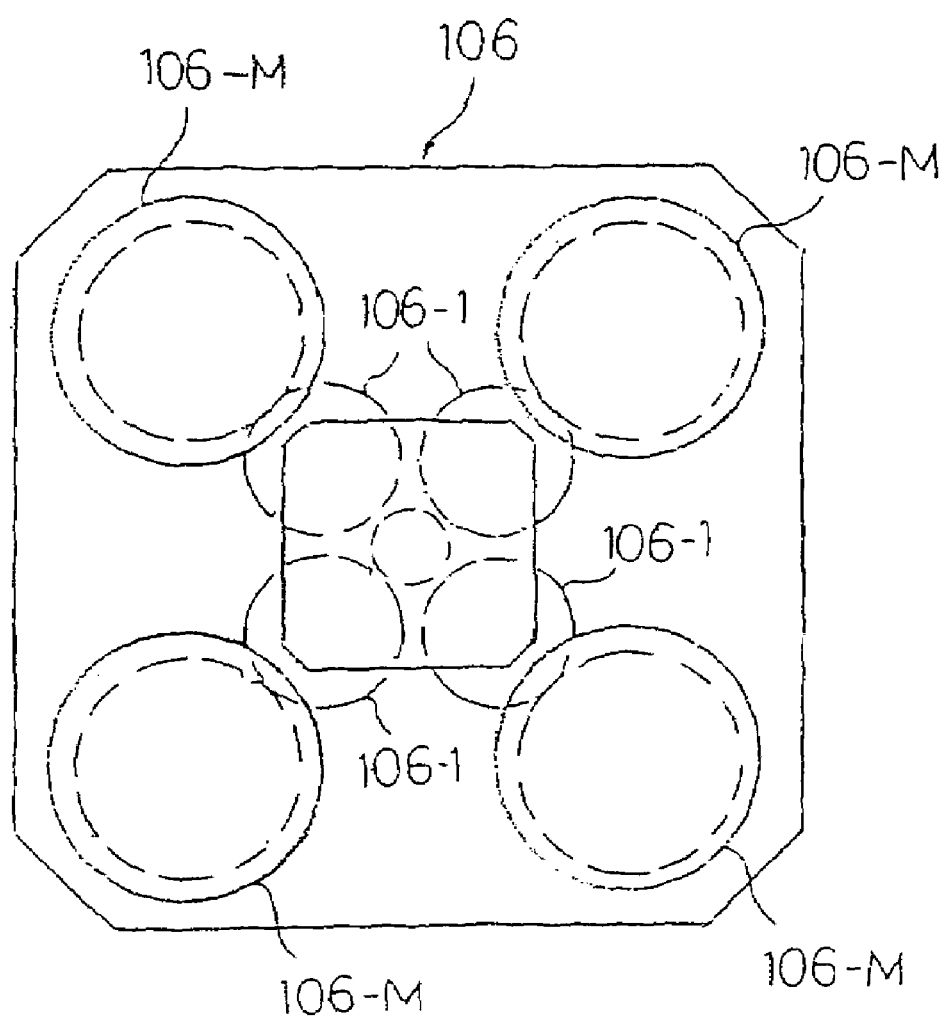
FIG. 18 is a top view of the capper shown in FIG. 17.

Referring to FIGS. 17 and 18, a detailed description will be given next to the structure of the capper 106.

The capper 106 shown in the drawings is for simultaneously performing the process of detaching or attaching a cap (lid) with respect to four tubes.

In FIGS. 17 and 18, the capper 106 has four collet chucks 106-1 . . . and each of the collet chucks 106-1 meshes with a cap not shown in the drawings to perform the operation of holding it. It is to be noted that only two of the collet chucks 106-1 are shown in FIG. 17 for simplified depiction.

Motors 106-M for the normal/reverse rotations of the respective collet chucks 106-1 . . . are disposed at positions offset from above the collet chucks 106-1 . . . in slightly sidewise directions.

As shown in FIG. 17, gears 106-MG are fastened to the respective rotation axes 106-MS of the motors 106-M. The gears 106-MG are engaged with the gears 106-1G to transmit the rotations of the motors 106-M to the collet chucks 106-1 via the respective shafts 106-1S of the collet chucks to which the gears 106-1G are fastened.

As shown in FIG. 18, there is no sufficient space to allow the placement of the four motors 106-M . . . immediately over the four collet chucks 106-1 . . . . This is why the motors 106-M are offset from the positions immediately over the respective collet chucks 106-1 in slightly sidewise directions by engaging the gears 106-1G provided on the respective shafts 106-1S of the collet chucks with the gears 106-MG fastened to the rotation shafts 106-MS of the motors.

Cylinders 106-S are provided at the centers of the motors 106-M. The cylinders 106-S vertically move members 106-2 for the expansion/contraction of (the collet chucks 106-1) attached to rods 106-R by vertically moving the rods 106-R and thereby contracting the collet chucks 106-1 (when the members 106-2 move downward) or expanding them (when the members 106-2 move upward).

When the rods 106-R move downward to lower the members 106-2 for extraction/compression, the end portions 106-2E of the members 106-2 come in contact with the tapered surfaces 106-1T of the collet chucks 106-1 to press the tapered surfaces 106-1T. As a result, the end portions 106-1E of the collet chucks 106-1 contract.

If the members 106-2 are moved upward by raising the rods 106-R, the pressing of the tapered surfaces 106-1T of the collet chucks 106-1 by the end portions 106-2E of the members 106-2 are released so that the end portions 106-1E of the collet chucks 106-1 expand from the contracted state to the state prior to contraction.

Bearings 106-3 are provided on the members 106-2 and slidably supporting the shafts 106-1S of the collet chucks 106-1. Under the action of such bearings 106-3, the rotating movements of the collet chucks 106-1 caused by the motors 106-M do not interfere at all with the cylinders 106-S and the contraction/expansion of the collet chucks 106-1 caused by the cylinders 106-S do not interfere with the transmission of the rotating movements of the motors 106-M.

A description will be given to an embodiment in which the capper 106 caps and uncaps tubes with reference mainly to FIG. 17.

In the case of opening caps from the tubes not shown, the rods 106-R and the members 106-2 are lowered by using the cylinders 106-S so that the end portions 106-2E of the members 106-2 press the tapered surfaces 106-1T of the collet chucks 106-1, whereby the collet chucks 106-1 contract to hold and fix caps not shown. In that state, the motors 106-M are rotated to rotate the collet chucks 106-1 in a cap opening direction and thereby uncap the tubes.

In the case of capping the tubes, collet chucks 106-1 holding the caps are aligned with the tubes so that the caps are positioned at the end portions of the tubes. If the motors are rotated in that state to rotate the caps in direction in which they are attached, the caps are screwed to the tubes. If the members 106-2 are raised by using the cylinders 106-S in that state, the collet chucks expand to be disengaged from the caps.

As described above, the detailed portion of the processing in the second embodiment of FIGS. 16 to 22 is the same as in the first embodiment but the second embodiment is different from the first embodiment in that four tubes are processed at a time in the case of FIGS. 16 to 22. Additionally, the second embodiment is also different from the first embodiment in that the capper 106, the piston pump 108, the separate injection nozzle 110, the large bead supplier 112, and the small bead supplier 114 move to positions in the vicinity of the work table 100, perform necessary processing with respect to the tubes in the rack 102, go away from the work table 100 after the processing, and return to the original positions shown in FIG. 16.

In the operation or processing in the second embodiment of FIGS. 16 to 22, four tubes are processed at a time and the tubes contained in the centrifugal separator 118 are placed in a low-temperature atmosphere, as stated previously. Consequently, the steps of "cooling the tube at 4° C." and holding it in the rack in the first embodiment of FIGS. 1 to 15, specifically Steps S15 and S24 of FIG. 13 and Step S35 of FIG. 14 are unnecessary in the second embodiment of FIGS. 16 to 22.

A description will be given next mainly to the state in which the foregoing devices come closer to the work table 100 and go away therefrom with reference to FIG. 16 and FIGS. 19 to 22.

Figure 19:
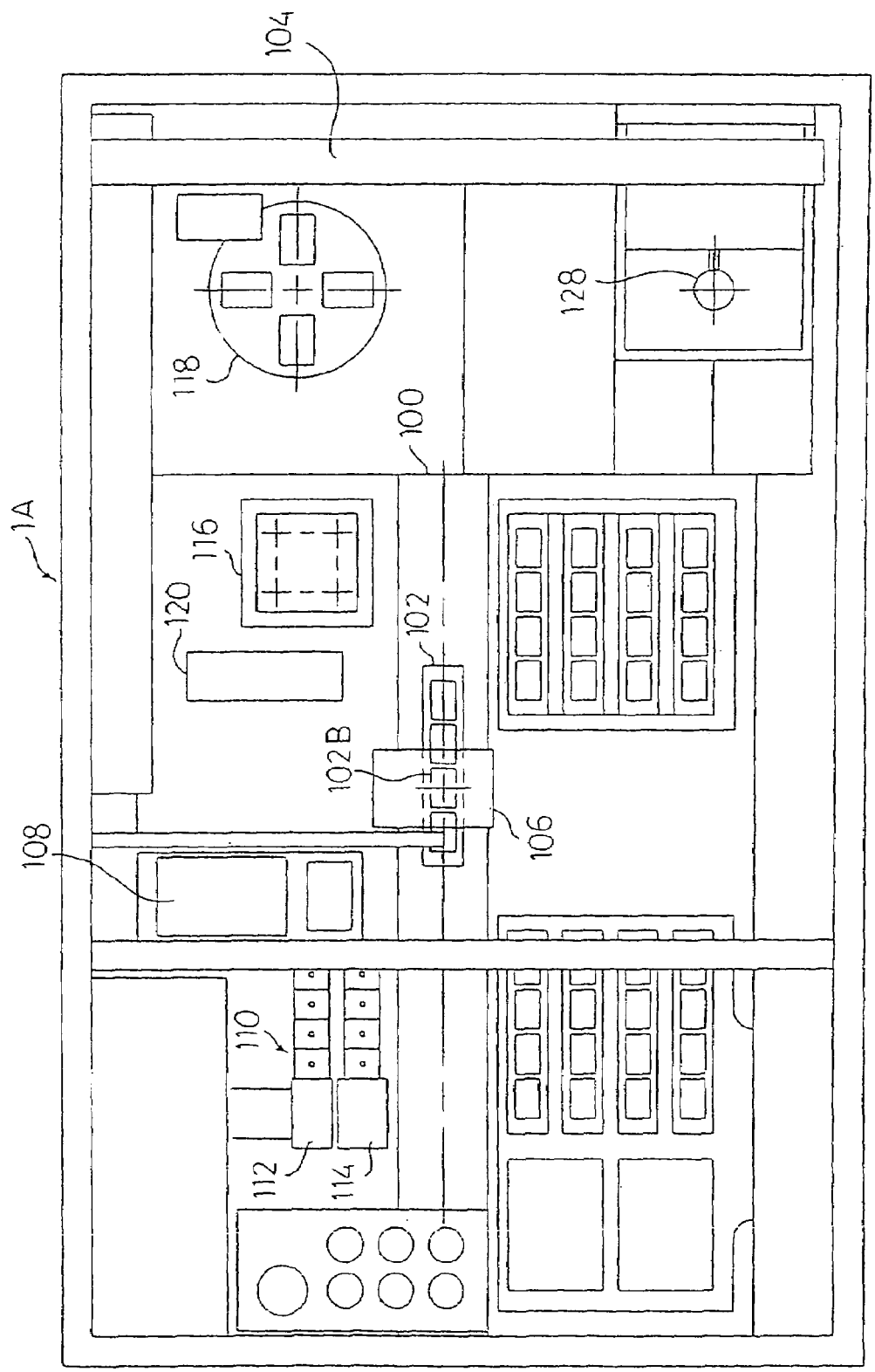
FIG. 19 is a top view showing a state in which a cap is detached from a tube by using the capper in the second embodiment.

First, in FIG. 19, the sample rack 102 has moved from the state shown in FIG. 16 to the left in the drawing and reached the position corresponding to the capper 106.

The capper 106 moves to a position over the work table 100 and simultaneously detaches four caps (not shown) disposed in the individual sections 102A to 102D of the sample rack 102.

The sample rack 102 is shifted to the left in the drawing by an amount corresponding to the length of the section and the capper 106 simultaneously uncaps the four tubes in each of the sections 102A, 102B, 102C, and 102D in this order on a per section basis. In FIG. 19, a state in which the capper 106 detaches the four caps from the section 102B is shown.

The process shown in FIG. 19 corresponds to Step S12 of FIG. 13 in the first embodiment of FIGS. 1 to 15.

In the case of capping the tubes also (corresponding to Step S13 of FIG. 13), the capper 106 moves to a position immediately over the work table 100 and the sample rack 102 is placed at a position corresponding thereto, as shown in FIG. 19.

Figure 20:
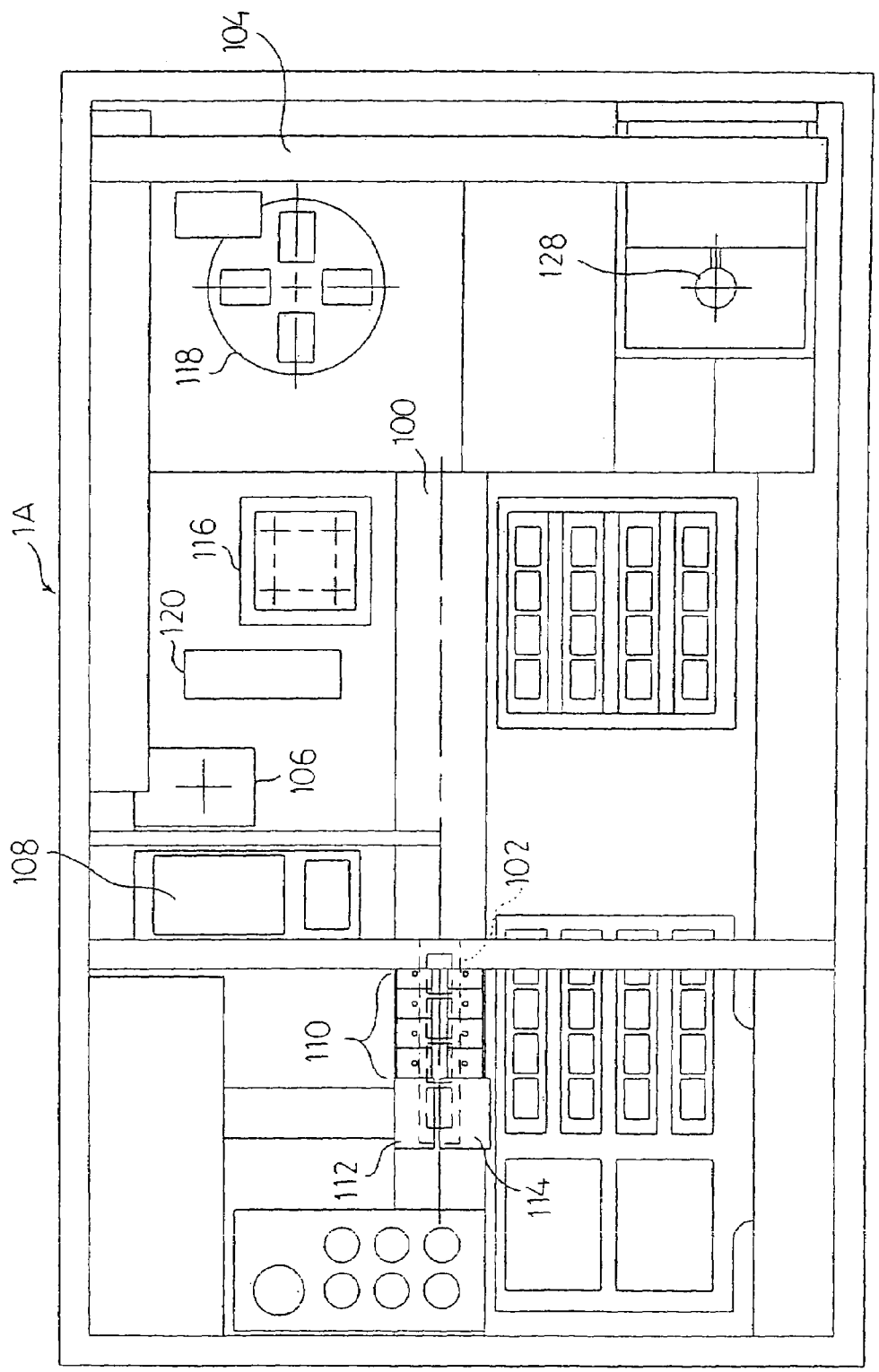
FIG. 20 is a top view showing a state in which a chemical is injected into a tube by using a separate injection nozzle in the second embodiment.

The state shown in FIG. 19, i.e., the state in which the four tubes are uncapped by using the capper 106 leads to the state shown in FIG. 20.

In FIG. 20, the sample rack 102 has moved to the position corresponding to the separate injection nozzle 110 and the separate injection nozzle 110 is in close proximity to the position immediately over the work table 100. By using the separate injection nozzle 110, a specified chemical agent is injected into the four tubes contained in each of the sections of the sample rack 102.

In the first embodiment of FIGS. 1 to 15, the process of injecting 1.0 ml of the PBS buffer in Step S12 of FIG. 13 corresponds to the state of FIG. 20. Otherwise, the process corresponding to Steps S18, S21, and S27 of FIG. 13 and Steps S32, S37A, S39, and the like of FIG. 14 corresponds to the state of FIG. 20 in the second embodiment of FIGS. 16 to 22.

In the second embodiment of FIGS. 16 to 22 also, large beads (e.g., beads having particle diameters of 2 mm to 3 mm) or small beads (beads having particle diameters of 0.1 mm) are supplied into the tubes in the same manner as in the large bead supply process (Step S12) or the small bead supply process (Step S21) in FIG. 13 of the first embodiment, though they are not shown in the drawings. In that case, the large bead supplier 112 or the small bead supplier 114 moves to the position immediately over each of the sections 102A to 102D of the sample rack 102 so that a relative relationship among the respective positions of the sample rack 102, the bead suppliers 112 or 114, and the separate injection nozzle 110 is similar to that among the positions shown in FIG. 20.

For a supernatant in each of the tubes to be sucked by using the piston pump 108 and discarded as shown in Step S17 of FIG. 13 in the second embodiment of FIGS. 16 to 22, it is necessary to preliminarily attach chips (placed on the chip placement area 134 of the table 138: See FIG. 16) to the tips of the piston pump 108.

Figure 21:
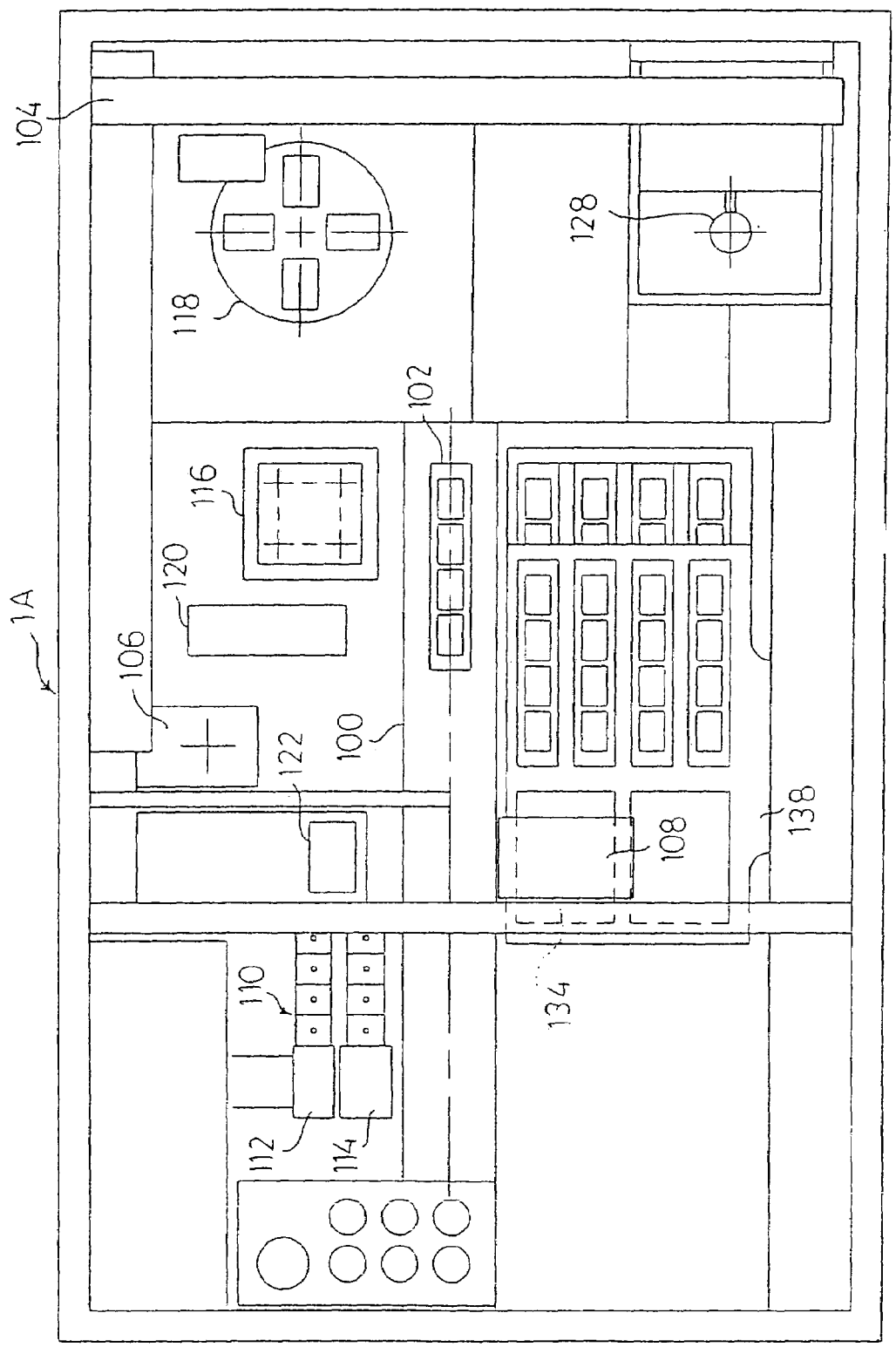
FIG. 21 is a top view showing a state in which chips are attached to the tips of a piston pump in the second embodiment.

FIG. 21 shows such a process. In the drawing, the table 138 moves to a position rightward of the position shown in FIG. 16 to move the chip placement area 134 to the position corresponding to the piston pump 108. If the piston pump 108 moves to the position immediately over the chip placement area 134, the state shown in FIG. 21 is reached.

Chips are attached individually to the four individual tips of the piston pump 108 in the state shown in FIG. 21, thought they are not shown distinctly.

Figure 22:
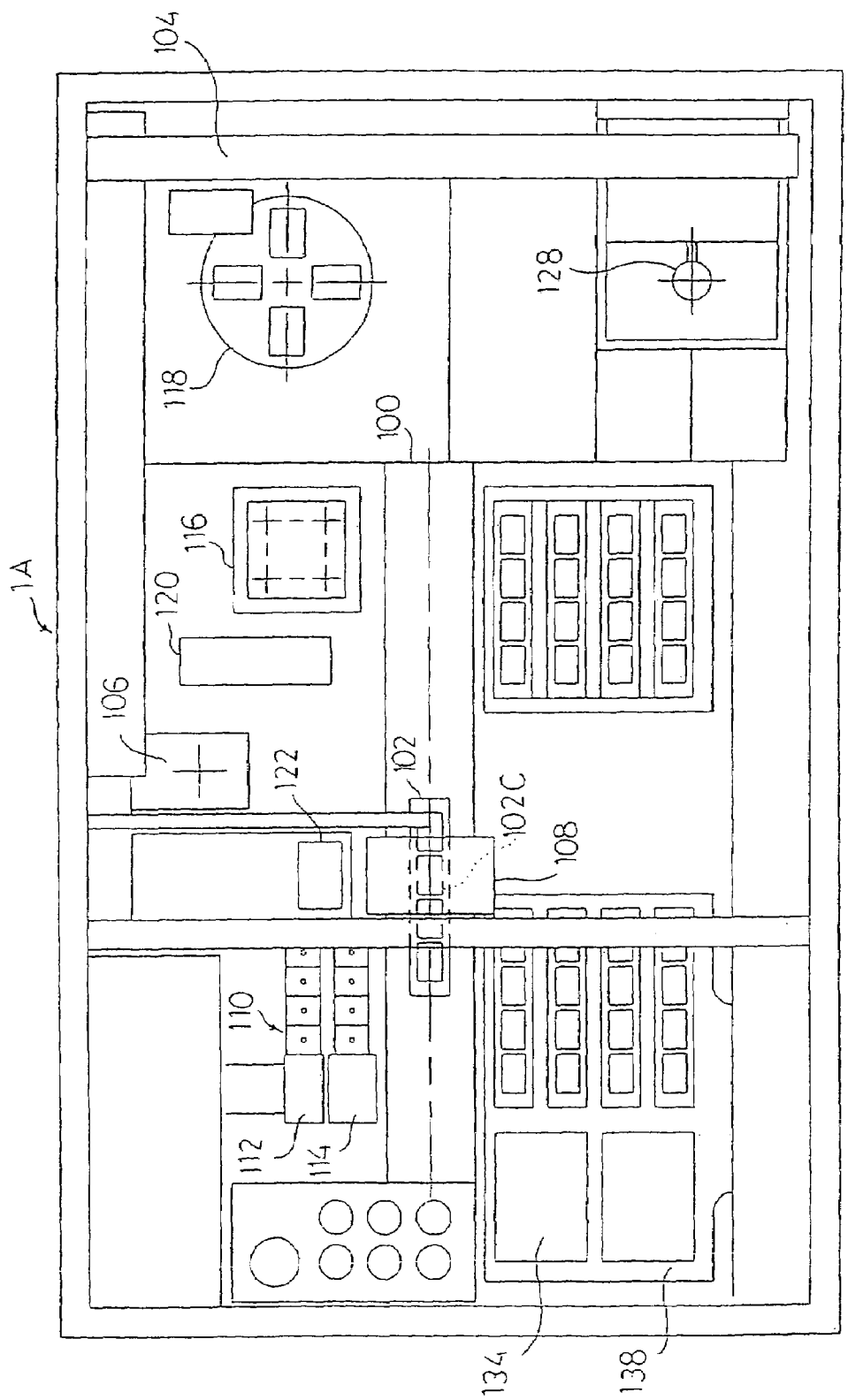
FIG. 22 is a top view showing a state in which a supernatant is removed by suction from tubes by using the piston pump in the second embodiment.

The attachment of the chips to the tips of the piston pump 108 brings about a state in which the supernatant can be sucked from the tubes so that the piston pump 108 is moved to the position immediately over the sample rack 102 by moving the sample rack 102, as shown in FIG. 22.

FIG. 22 shows the state in which the supernatant in each of the four tubes contained in the section 102C of the sample rack 102, which are not shown, is sucked by using the piston pump 108. The state shown in FIG. 22 corresponds to, e.g., the process of Steps S17 and S26 of FIG. 13 and Step S37 of FIG. 14.

The supernatant sucked in the state shown in FIG. 22 is discarded together with the chips not shown into the vessel 122 (for the disposal of the liquid waste and the discarded chips), though it is not depicted.

In the second embodiment of FIGS. 16 to 22, the timing of the movement of the sample rack 102 over the work table 100 with the movements of the individual devices (the capper 106, the piston pump 108, the separate injection nozzle 110, the large bead supplier 112, and the small bead supplier 114) and the alignment of the sample rack 102 with the individual devices are performed based on detection signals from various position detecting sensors or by determining a timing in tune with a clock pulse.

However, it is also possible to perform such timing determination and alignment by using other well-known techniques. In other words, it is not intended to particularly limit such control.

It is to be noted that the embodiments shown in the drawings are only illustrative and the foregoing description does not intend to restrict the technical scope of the present invention.

For example, although the embodiments shown in the drawings have described the type which individually processes tubes on a one-by-one basis (FIGS. 1 to 15) and the type which processes four tubes at a time (FIGS. 16 to 22), the number of the tubes processed simultaneously is not limited thereto.

EFFECT OF THE INVENTION

The operation/working-effect of the present invention will be listed herein below.

(1) In accordance with the present invention, a shaker, a centrifugal separator, particle suppliers, a liquid chemical supply mechanism, a tube conveying arm, and control means for controlling these units such that a nucleic acid is extracted automatically are formed integrally so as to allow automatic control. This facilitates scaling down and allows short-time and reliable extraction of the nucleic acid even from a specimen from which it has conventionally been considered difficult to extract the nucleic acid.

(2) Since the control means according to the present invention accomplishes the extraction of the nucleic acid by placing large-diameter particles (beads) and a specimen in a tube, subjecting the tube to shaking and centrifugal separation to separate a fungus body containing the nucleic acid, shaking the separated fungus body together with small-diameter particles, and crushing the fungus body by centrifugal separation, it is possible to reliably remove impurities and precisely extract only the nucleic acid in a short period of time.

(3) Since the control means according to the present invention separates the nucleic acid by crushing the material containing the nucleic acid, dries the separated nucleic acid by using alcohol, and purifies the dried nucleic acid by gel filtration chromatography, the nucleic acid is dried fast by the evaporation of alcohol and the moving speed of the nucleic acid is increased by gel filtration chromatography, which achieves a reduction in nucleic acid extraction time.

(4) Since the supply mechanism for large-diameter particles (beads) has particles agitating means provided in a particle storage unit (hopper), the large-diameter particles (beads) are allowed to fall into a supply path to be supplied without causing a jam in a trench in the supplier.

(5) In the supply mechanism for small-diameter particles (beads), a particle storage unit (hopper) and a measurement unit are provided in contact relation and the flowing of the small-diameter particles into the measurement unit and the flowing and supply thereof from the measurement unit to the outside are performed simultaneously by a single upward and downward movement of a valve, which ensures precise measurement and the flowing and supply of the small-diameter particles.

What is claimed is:

1. A nucleic acid extraction apparatus including: a shaker; a centrifugal separator; a supplier for large beads and another supplier for small beads; a liquid chemical supply mechanism for supplying a liquid chemical; an arm for conveying a specimen or a tube having therein the specimen; and control means, wherein the control means is constructed to perform a control operation for shaking the tube supplied with particles each having a large particle diameter and the specimen, putting the tube through the centrifugal separator to separate a material containing a nucleic acid from the specimen, shaking the tube supplied with the separated material containing the nucleic acid and particles each having a small particle diameter, and putting the tube through the centrifugal separator to crush the material containing the nucleic acid and extract the nucleic acid, wherein the supplier for large beads has a rotating member formed with a cavity portion having a capacity corresponding to a quantity of supplied particles and disposed in a supply path, the supply path is extending in a vertical direction and connecting to a passage underlying a storage unit for storing particles to be supplied, and particle agitating means is provided rotatably in said storage unit, so that large beads are filled in the cavity portion in a case that the rotating member rotates and the passage underlying a storage unit connects to the cavity portion formed in the rotating member, and then large beads fall to be supplied through the supply path when the rotating member rotates and the cavity portion formed in the rotating member connects to the supply path positioned under the cavity portion; and wherein the supplier for small beads has a measurement unit for measuring the quantity of the supplied particles, a supply unit provided under the measurement unit, a particle storage unit provided over the measurement unit, a sheet unit formed on a boundary between the particle storage unit and the measurement unit, a valve constructed to be vertically movable, open said sheet unit and close an inlet of said supply unit when it moves downward and close said sheet unit and open the inlet of said supply unit when it moves upward, and means for vertically moving the valve, so that small beads flow into the measurement unit in case that the valve moves downward and open said sheet unit, and then small beads are fallen and supplied from supply unit when the valve moves upward and open the inlet of the supply unit.

2. A nucleic acid extraction apparatus according to claim 1, wherein said control means is constructed to perform a control operation for separating the nucleic acid by crushing the material containing the nucleic acid, recovering the separated nucleic acid, and purifying the recovered nucleic acid by gel filtration chromatography.

3. A nucleic acid extraction apparatus according to claim 1 or 2, wherein said centrifugal separator has a stop position indicating member disposed in correspondence with a specified stop position, indicating member detecting means for detecting the stop position indicating member being at the specified position, driving means for moving, when the stop position indicating member does not stop at the specified position, the stop position indicating member to the stop position, and a rotation transmission mechanism.

4. A nucleic acid extraction apparatus having: a shaker; a centrifugal separator; a supplier for large beads and another supplier for small beads; a liquid chemical supply mechanism for supplying a liquid chemical; a lid attachment/detachment unit for attaching and detaching a lid to and from each of tubes; and a work table, wherein specimens or a plurality of the tubes having therein the specimens are contained in respective sections of a tube containing member, the tube containing member can be moved by moving means over the work table, said shaker, the centrifugal separator, the particle supply mechanism, the liquid chemical supply mechanism, and the lid attachment/detachment unit are constructed to be capable of simultaneously processing the plurality of tubes, and said particle supply mechanism, the liquid chemical supply mechanism, and the lid attachment/detachment unit are constructed to be movable between a position immediately over said work table when giving necessary processing to the tubes in the tube containing member and a position at a distance from said work table, said nucleic acid extraction apparatus including control means, wherein said control means is constructed to perform a control operation for shaking the tubes supplied with particles each having a large particle diameter and the specimens, putting the tubes through the centrifugal separator to separate a material containing a nucleic acid from each of the specimens, shaking the tubes supplied with the separated material containing the nucleic acid and particles each having a small particle diameter, and putting the tubes through the centrifugal separator to crush the material containing the nucleic acid and extract the nucleic acid, wherein the supplier for large beads has a rotating member formed with a cavity portion having a capacity corresponding to a quantity of supplied particles and disposed in a supply path, the supply path is extending in a vertical direction and connecting to a passage underlying a storage unit for storing particles to be supplied, and particle agitating means is provided rotatably in said storage unit, so that large beads are filled in the cavity portion in a case that the rotating member rotates and the passage underlying a storage unit connects to the cavity portion formed in the rotating member, and then large beads fall to be supplied through the supply path when the rotating member rotates and the cavity portion formed in the rotating member connects to the supply path positioned under the cavity portion; and wherein the supplier for small beads has a measurement unit for measuring the quantity of the supplied particles, a supply unit provided under the measurement unit, a particle storage unit provided over the measurement unit, a sheet unit formed on a boundary between the particle storage unit and the measurement unit, a valve constructed to be vertically movable, open said sheet unit and close an inlet of said supply unit when it moves downward and close said sheet unit and open the inlet of said supply unit when it moves upward, and means for vertically moving the valve, so that small beads flow into the measurement unit in case that the valve moves downward and open said sheet unit, and then small beads are fallen and supplied from supply unit when the valve moves upward and open the inlet of the supply unit.

* * * * *